US009562079B2

(12) United States Patent
Lohse et al.

(10) Patent No.: US 9,562,079 B2
(45) Date of Patent: Feb. 7, 2017

(54) VACCINES AND METHODS TO TREAT LYME DISEASE IN DOGS

(71) Applicants: Zoetis LLC, Florham Park, NJ (US); Virginia Commonwealth University, Richmond, VA (US)

(72) Inventors: Robert M. Lohse, Kalamazoo, MI (US); Patrick F. M. Meeus, Richland, MI (US); Jason J. Millership, Portage, MI (US); Zhichang Xu, Kalamazoo, MI (US); Richard Thomas Marconi, Midlothian, VA (US); Christopher G. Earnhart, Spotsylvania, VA (US)

(73) Assignees: Zoetis Services LLC, Parsippany, NJ (US); Virginia Commonwealth University, Richmond, VA (US)

( * ) Notice: Subject to any disclaimer, the term of this patent is extended or adjusted under 35 U.S.C. 154(b) by 184 days.

(21) Appl. No.: 13/864,658

(22) Filed: Apr. 17, 2013

(65) Prior Publication Data

US 2014/0314801 A1 Oct. 23, 2014
US 2016/0083435 A9 Mar. 24, 2016

Related U.S. Application Data

(60) Provisional application No. 61/635,031, filed on Apr. 18, 2012.

(51) Int. Cl.

| | |
|---|---|
| ***C07K 14/20*** | (2006.01) |
| ***A61K 39/02*** | (2006.01) |
| *A61K 39/00* | (2006.01) |

(52) U.S. Cl.

CPC ........... *C07K 14/20* (2013.01); *A61K 39/0225* (2013.01); *A61K 2039/552* (2013.01); *A61K 2039/55505* (2013.01); *A61K 2039/70* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 6,197,301 | B1 | 3/2001 | Flavell et al. | |
| 6,210,676 | B1 | 4/2001 | Callister et al. | |
| 6,464,985 | B1 | 10/2002 | Callister et al. | |
| 6,676,942 | B1 * | 1/2004 | Lobet et al. | 424/190.1 |
| 6,872,550 | B1 | 3/2005 | Livey et al. | |
| 7,179,448 | B2 | 2/2007 | Dattwyler et al. | |
| 7,794,727 | B2 | 9/2010 | Marconi et al. | |
| 2007/0178117 | A1 | 8/2007 | Marconi et al. | |
| 2009/0297560 | A1 | 12/2009 | Dattwyler et al. | |
| 2011/0070257 | A1 | 3/2011 | Marconi et al. | |
| 2011/0262475 | A1 | 10/2011 | Earnhart et al. | |
| 2013/0266606 | A1 | 10/2013 | Marconi et al. | |

FOREIGN PATENT DOCUMENTS

| | | | |
|---|---|---|---|
| WO | 9304175 | A1 | 3/1993 |
| WO | 0006745 | | 2/2000 |
| WO | 0078966 | A1 | 12/2000 |
| WO | 2009/135118 | | 11/2009 |
| WO | 2010132758 | A2 | 11/2010 |
| WO | 2012/054580 | | 4/2012 |

OTHER PUBLICATIONS

Buckles et al., "Analysis of Antibody Response in Humans to the Type A OspC Loop 5 Domain and Assessment of the Potential Utility of the Loop 5 Epitope in Lyme Disease Vaccine Development", Clinical and Vaccine Immunology, 13(10):1162-1165, 2006.

Earnhart et al., "Demonstration of OspC Type Diversity in Invasive Human Lyme Disease Isolates and Identification of Previously Uncharacterized Epitopes That Define the Specificity of the OspC Murine Antibody Response", Infection and Immunity, 73(12):7869-7877, 2005.

Jones et al., "Analysis of Borrelia burgdorferi Genotypes in Patients With Lyme Arthritis", Arthritis & Rheumatism, 60 (7):2174-2182, 2009.

Kumaran et al., "Crystal structure of outer surface protein C (OspC) from the Lyme disease spirochete, Borrelia burgdorferi", The EMBO Journal, 20(5):971-978, 2001.

Lovrich et al., "Borreliacidal OspC Antibody Response of Canines with Lyme Disease Differs Significantly from That of Humans with Lyme Disease", Clinical and Vaccine Immunology, 14(5):635-637, 2007.

Seinost et al., "Four Clones of Borrelia burgdorferi Sensu Stricto Cause Invasive Infection in Humans", Infection and Immunity, 67(7):3518-3524, 1999.

Buckles et al., "Analysis of Antibody Response in Humans," Clinical & Vaccine Immunology, Oct. 2006, pp. 1162-1165.

Chothia et al., "The relation between the divergence of sequence and structure in proteins," The EMBO Journal, vol. 5, No. 4, 1986, pp. 823-826.

Earnhart et al., "Development of an OspC-based tetravalent, recombinant, chimeric vaccinogen that elicits bactericidal antibody against diverse Lyme disease spirochete strains," Vaccine, Jan. 5, 2007, vol. 25, No. 3, pp. 466-480.

Earnhart et al., "OspC Phylogenetic Analyses Support the Feasibility of a Broadly Protective Polyvalent Chimeric Lyme Disease Vaccine," Clinical and Vaccine Immunology, vol. 14, No. 5, Mar. 14, 2007, pp. 628-634.

Earnhart et al., "Construction and analysis of variants of a polyvalent Lyme disease vaccine: approaches for improving the immune response to chimeric vaccinogens," Vaccine, Apr. 20, 2007, vol. 25, No. 17, pp. 3419-3427.

Earnhart et al., "An Octavalent Lyme Disease Vaccine Induces Antibodies that Recognize all Incorporated OspC Type-Specific Sequences," Human Vaccines, Nov. 1, 2007, vol. 3, No. 6, pp. 281-289.

(Continued)

*Primary Examiner* — Gary Nickol
*Assistant Examiner* — Khatol Shahnan Shah
(74) *Attorney, Agent, or Firm* — Vyacheslav Vasilyev

(57) ABSTRACT

The instant invention provides an immunogenic composition comprising an antigenic fragment of OspA protein of *Borrelia burgdorferi* and a chimeric protein containing antigenic fragments of different phylotypes of OspC protein of *Borrelia burgdorferi*. Vaccines incorporating the immunogenic composition of the invention, as well as methods of preventing Lyme disease in dogs and/or protecting dogs from Lyme disease using the vaccines are also provided.

23 Claims, 7 Drawing Sheets

(56) References Cited

OTHER PUBLICATIONS

Greenspan et al., "Defining epitopes: It's not as easy as it seems," Nature Biotechnology, vol. 17, Oct. 1999, pp. 936-937.

Ivanova et al., "Comprehensive seroprofiling of sixteen B. burgdorferi OspC: Implications for Lyme disease diagnostics design," Clinical Immunology, Academic Press, U.S., vol. 132, No. 3, Sep. 1, 2009, pp. 390-400.

PCT International Search Report mailed in connection with international application, PCT/US2013/037063, filed Apr. 18, 2013.

Probert, "Protection of C3H/HeN Mice from Challenge with Borrelia burgdorferi through Active Immunization with OspA, OspB, or OspC, but Not with OspD or the 83-Kilodalton Antigen," Infection and Immunity, vol. 62, No. 5, May 1994, pp. 1920-1926.

Rhodes et al., "Identification of Borrelia burgdorferi ospC genotypes in canine tissue following tick infestation: implications for Lyme disease vaccine and diagnostic assay design," The Veterinary Journal, vol. 198, No. 2, Aug. 17, 2013, pp. 412-418.

Wallich et al., "DNA Vaccines Expressing a Fusion Product of Outer Surface Proteins A and C from Borrelia burgdorferi Induce Protective Antibodies Suitable for Prophylaxis but Not for Resolution of Lyme Disease," Infection and Immunity, vol. 69, No. 4, Apr. 2001, pp. 2130-2136.

* cited by examiner

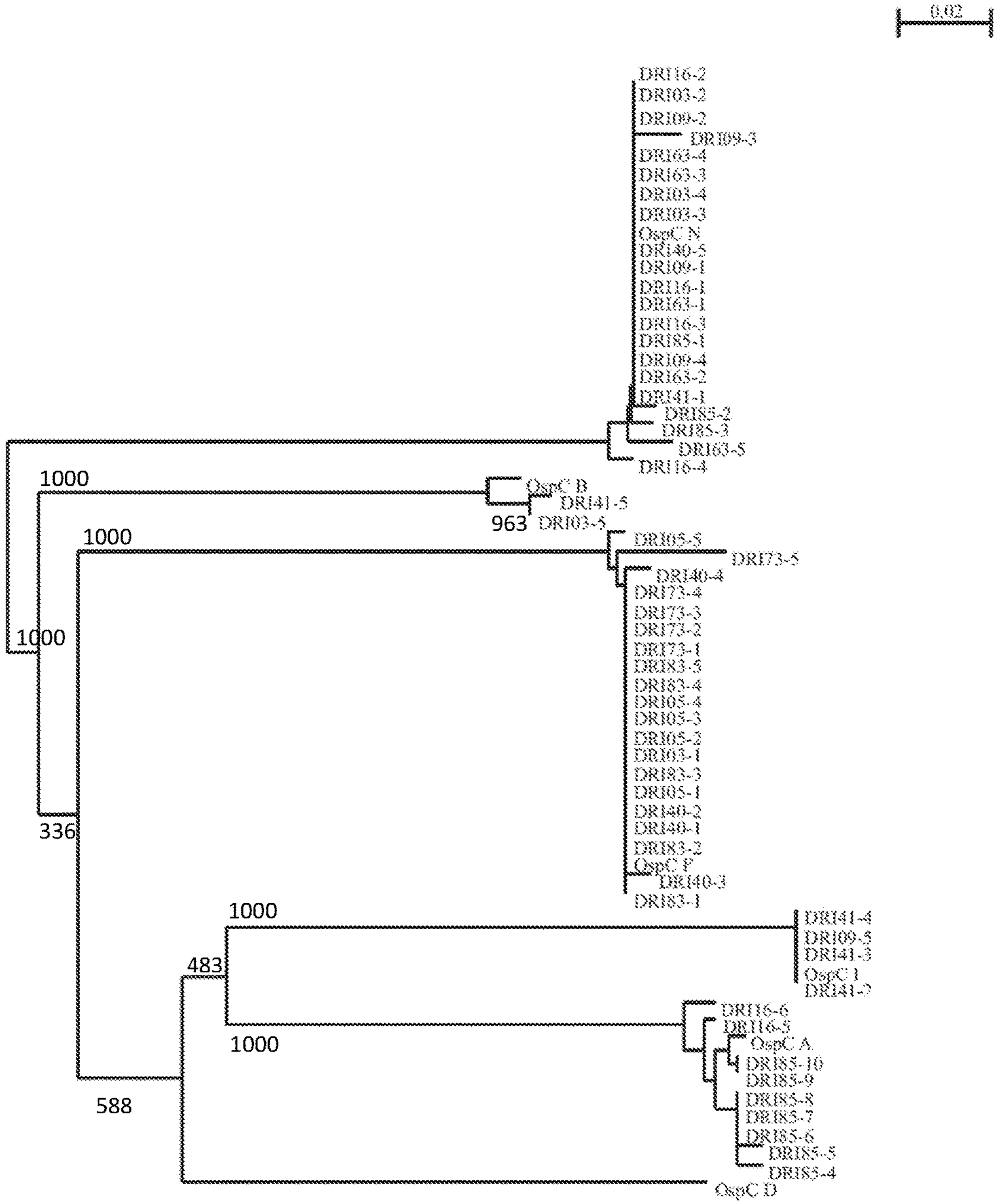
FIG. 1: Skin Biopsy Sequencing Tree

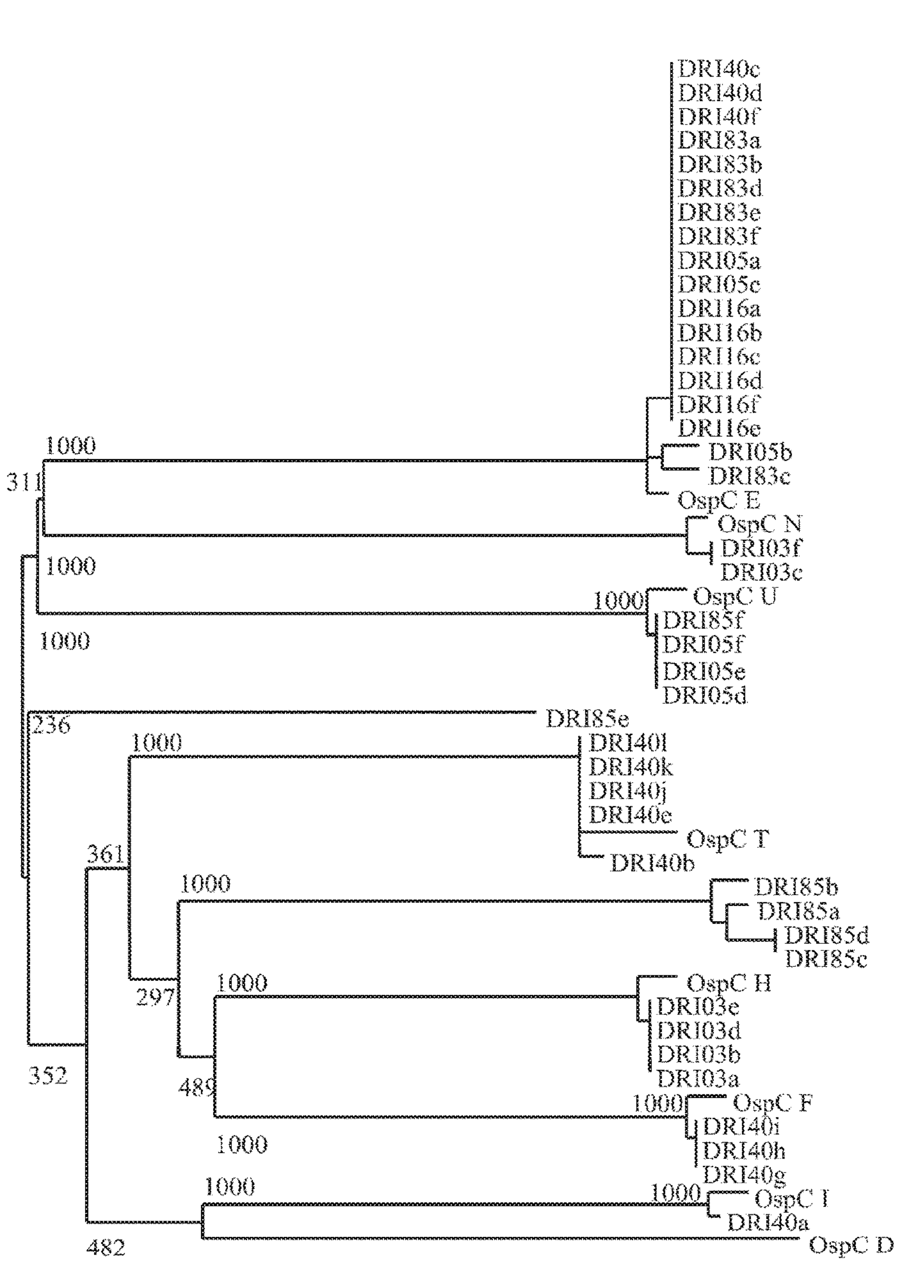
FIG. 2: B burgorferi clone Sequencing

FIG. 3A

AKLKGEHTDLGKEGVTKGADELEKLFESVKNLSKAAKEMLTNSVKESEKFAGK
<--------------lpI--------------><----------------------hxI-----------------------------><----------

LKNEHASLGKKDATKGAKELKDLSDSVESLVKASDDFTKKLQSSHAQLGVAGG
-------lpH------------------><---------------hxH-------------><------------------lpN-------------

ATTADELEKLFKSVESLAKAAQDALANSVNELTSKKLKEKHTDLGKKDATAAE
----><--------------------------hxN---------------------------><-------------lpC------------><---

LEKLFESVENLAKAAKEMLSNSNKAFTDKLKSSHAELGIANGAATKGAQELEKL
-----------------hxC------------------><----------------------lpM---------------------><--------------

FESVKNLSKAAQETLNNSVKESESFTKKLSDNQAELGIENATKGAEELVKLSESV
--------hxM-------------------------------><-------------lpD-----------------><-----------------------

AGLLKAAQAILANSVKELTSPVVAESPKKPNNSGKDGNTSANSADESVKGPNL
------------------hxC----------------------------------------><----------------------------------------------

TEISKKITESNAVVLAVKEIETLLSSIDELATKAIGQKIDANGLGVQANQNGSLLA
-----------------------------------------------------------------------------------------------------------

GAYAISTLITQKLSALNSEDLKEKVAKVKKCSEDFTNKLKNGNAQLGLAAATDD
---------------OspC Type F--------------------------------------------------------------------------------

31

NAKAAILKTNGTNDKGAKELKDLSD LVKAAQVMLTNSVKELTSPVVAES
-----------------------------------------------------------------------------------------------------------

PKKP (SEQ ID NO: 31)
--------->

FIG. 3B

```
SEDFTNKLKNGNAQLGLAAATKGAKELKDLSDSVESLVKAAQVMLTNSSTGFT
<--------------lpF----------------------><-----------------------hxF----------------------><------

NKLKSGHAELGPVGGNATKGAKELKDLSESVEALAKAAQAMLTNSSEKFTKKL
-----lpT--------------------------><--------------------hxT-------------------------><------------

SESHADIGIQAATKGAEELDKLFKAVENLSKSTEFTNKLKSEHAVLGLDNLTKG
--lpU------------------><-------------hxU--------------><----------------lpE------------------><--

AAELEKLFKAVENLSKAAQDTLKNAVKELTSPIVAESPKKPSETFTNKLKEKHT
-------------------------------hxE--------------------------------------------><-------------lpA-----

DLGKEGVTKGAEELGKLFESVEVLSKAAKEMLANSVKELTSSEEFSTKLKDNHA
----------------><--------------------hxA-----------------------------------><----------lpB--------

QLGIQGVTKGVEELEKLSGSLESLSSEDFTKKLEGEHAQLGIENVTAAELEKLFK
----------------><------------hxB-----------><----------------lpK----------------><---------------

AVENLAKAAKEMAKLKGEHTDLGKEGVTKGADELEKLFESVKNLSKAAKEML
hxK-------------------><-----------lpI----------------><--------------------hxI-------------------

TNSVKESEKFAGKLKNEHASLGKKDATKGAKELKDLSDSVESLVKASDDFTKK
-----------><-----------------lpH------------------><---------------hxH---------------><-----------

LQSSHAQLGVAGGATTADELEKLFKSVESLAKAAQDALANSVNELTSKKLKEK
------lpN----------------------><-------------------------hxN---------------------------><---------

HTDLGKKDATAAELEKLFESVENLAKAAKEMLSNSNKAFTDKLKSSHAELGIA
--lpC--------------><--------------------hxC----------------------><----------------lpM------------

NGAATKGAQELEKLFESVKNLSKAAQETLNNSVKESESFTKKLSDNQAELGIEN
----------><-------------------------hxM-------------------------><---------------lpD--------------

ATKGAEELVKLSESVAGLLKAAQAILANSVKELTSPVVAESPKKPNNSGKDGNT
---><---------------------------------------hxD-----------------------------------><---------------

SANSADESVKGPNLTEISKKITESNAVVLAVKEIETLLSSIDELATKAIGQKIDAN
---------------------------------------------------------------------------------------OspC Type F----

GLGVQANQNGSLLAGAYAISTLITQKLSALNSEDLKEKVAKVKKCSEDFTNKLK
----------------------------------------------------------------------------------------------------

NGNAQLGLAAATDDNAKAAILKTNGTNDKGAKELKDLSDSVESLVKAAQVML
----------------------------------------------------------------------------------------------------

TNSVKELTSPVVAESPKKP          (SEQ ID NO: 30)
------------------------------------>
```

FIG. 4A

OspC phylotype A (Strain B31) – Genbank accession no. AAC66329

SEQ ID NO: 35

```
  1 mkkntlsail  mtlflfiscn  nsgkdgntsa  nsadesvkgp  nlteiskkit
    dsnavllavk
 61 eveallssid  eiaakaigkk  ihqnngldte  nnhngsllag  ayaistlikq
    kldglknegl
121 kekidaakkc  setftnklke  khtdlgkegv  tdadakeail  ktngtktkga
    eelgklfesv
181 evlskaakem  lansvkelts  pvvaespkkp
```

OspC phylotype B (strain LDP973) – Genbank accession no. ABK41066

SEQ ID NO: 36

```
  1 nnsgkdgnts  ansadesvkg  pnlteiskki  tdsnavllav  keveallssi
    delakaigkk
 61 ikndgsldne  anrnesllag  aytistlitq  klsklngseg  lkekiaaakk
    cseefstklk
121 dnhaqlgiqg  vtdenakkai  lkanaagkdk  gveeleklsg  sleslskaak
    emlansvkel
181 tspvvaespk  kp
```

OspC phylotype D (strain LDP116) – Genbank accession no. ABK41068

SEQ ID NO: 37

```
  1 nnsgkdgnts  ansadesvkg  pnlteiskki  tdsnavllav  kevevllssi
    delakkaigk
 61 kidqnnalgt  lnnhngslla  gayaisalit  eklssikdsg  elkaeiekak
    kcsesftkkl
121 sdnqaelgie  natddnakka  ilkthnakdk  gaeelvklse  svagllkaaq
    ailansvkel
181 tspvvaespk  kp
```

OspC phylotype E (strain N40) – Genbank accession no. AAQ19279

SEQ ID NO: 38

```
  1 cnnsgkdgna  sansadesvk  gpnlteiskk  itesnavvla  vkevetllas
    idelatkaig
 61 kkignnglea  nqskntslls  gayaisdlia  eklnvlknee  lkekidtakq
    csteftnklk
121 sehavlgldn  ltddnaqrai  lkkhankdkg  aaeleklfka  venlskaaqd
    tlknavkelt
181 spivaes
```

FIG. 4B

OspC phylotype F (strain PAd) – Genbank accession no. AAQ19283

SEQ ID NO: 39

```
  1 cnnsgkdgnt  sansadesvk gpnlteiskk  itesnavvla  vkeietllss
    idelatkaig
 61 qkidanglgv  qanqngslla gayaistlit  qklsalnsed  lkekvakvkk
    csedftnklk
121 ngnaqlglaa  atddnakaai lktngtndkg  akelkdlsds  veslvkaaqv
    mltnsvkelt
181 spvvaes
```

OspC phylotype H (strain LDS101) – Genbank accession no. ABK41065

SEQ ID NO: 40

```
  1 nnsgkdgnts  ansadesvkg pnlteiskki  tesnavvlav  kevetllasi
    nqlakaigkk
 61 idqngtlgdd  ggqngsllag ayaistviie  klstlknvee  lkekitkakd
    csekfagklk
121 nehaslgkkd  atdddakkai lkthgntdkg  akelkdlsds  veslvkaake
    mltnsvkelt
181 spvvaespkk  p
```

OspC phylotype I (strain HB19) – Genbank accession no. AAC43297

SEQ ID NO: 41

```
  1 mkkntlsail  mtlflfiscn nsgkdgntsa  nsadesvkgp  nlteiskkit
    esnavvlavk
 61 evetlltsid  elakaigkki kndvsldnea  dhngslisga  ylistlitkk
    isaikdsgel
121 kaeiekakkc  seeftaklkg ehtdlgkegv  tddnakkail  ktnndktkga
    deleklfesv
181 knlskaakem  ltnsvkelts pvvaespkkp
```

OspC phylotype K (strain LDP74) – Genbank accession no. ABK41058

SEQ ID NO: 42

```
  1 nnsgkdgnts  ansadesvkg pnlteiskki  tesnavvlav  keietllasi
    delatkaigk
 61 kiqqngglav  eaghngtlla gaytisklit  qkldglknse  klkekienak
    kcsedftkkl
121 egehaqlgie  nvtdenakka ilitdaakdk  gaaeleklfk  avenlakaak
    emlansvkel
181 tspivaespk  kp
```

FIG. 4C

OspC phylotype L (strain SI1) – Genbank accession no. AAK69466
SEQ ID NO: 43

```
  1 sailmtlflf  iscnnsgkdg nasvnsades   vkgpnlveis  kkitdsnavv
    iavkevetll
 61 vsidelakai  gkkieaggtl gsdgahngsl   lagaykiate  itanlsklka
    sedlkekitk
121 akecsekftd  klksenaalg kqdasdddak   kailkthndi  tkgakelkel
    sesvetllka
181 akemlansvk  eltspvvakn pk
```

OspC phylotype M (strain B356) – Genbank accession no. AAN37936
SEQ ID NO: 44

```
  1 mkkntlsail  mtlflfiscn nsgkdgntsa   nsadesvkgp  nlteiskkit
    esnavvlavk
 61 evetllasid  evakkaignl iaqnglnaga   nqngsllaga  yvistliaek
    ldglknseel
121 kekiedakkc  nkaftdklks shaelgiang   aatdanakaa  ilktngtkdk
    gaqeleklfe
181 svknlskaaq  etlnnsvkel tspvvaespk   kp
```

OspC phylotype N (strain LDP63) – Genbank accession no. ABK41056
SEQ ID NO: 45

```
  1 nnsgkdgnas  tnsadesvkg pnlteiskki   tesnavvlav  kevaallssi
    delakaigkk
 61 innnglddvq  nfnasllaga htisklvtek   lsklknsegl  kekiedakkc
    sddftkklqs
121 shaqlgvagg  attdeeakka ilrtnaikdk   gadeleklfk  sveslakaaq
    dalansvnel
181 tspvvaespk  kp
```

OspC phylotype U (strain 148) – Genbank accession no. AAQ19278
SEQ ID NO: 46

```
  1 cnnsgkdgna  sansadesvk gpnlaeiskk   itesnavvla  vkeveallas
    ideigskaig
 61 kriqanglqd  lqgqngslla gayaisnlit   qkinvlnglk  nseelkekin
    eakgcsekft
121 kklseshadi  giqaatdana kdailktnpt   ktkgaeeldk  lfkavenlsk
    aakemlansv
181 keltspvvae  s
```

VACCINES AND METHODS TO TREAT LYME DISEASE IN DOGS

FIELD OF THE INVENTION

This invention is in the field of veterinary medicine. More particularly, this invention is in the field of vaccines treating or preventing Lyme disease in dogs.

BACKGROUND

Lyme disease is a bacterial infection caused by pathogenic spirochetes of the genus *Borrelia*. The infection can occur in humans, dogs, deer, mice and other animals, and is transmitted by arthropod vectors, most notably ticks of the genus *Ixodes*. *Borrelia burgdorferi*, the most common cause of Lyme disease in North America, was first cultured in 1982. *Borrelia* are introduced into the host at the site of the tick bite and this is also the location of the initial characteristic skin lesion, erythema chronicum migrans (ECM). In dogs, Lyme disease manifests with arthritis-induced lameness, anorexia, fever, lethargy, lymphadenopathy, and in some cases, fatal glomerulonephritis. A recent study revealed that the percentage of actively infected dogs in endemic areas can be as high as 11%.

The infection may be treated at any time with antibiotics such as penicillin, erythromycin, tetracycline, and ceftriaxone. Once infection has occurred, however, the drugs may not purge the host of the spirochete, but may only act to control the chronic forms of the disease. Complications such as arthritis and fatigue may continue for several years after diagnosis and treatment.

The canine Lyme disease vaccines were developed to provide protection by primarily inducing OspA borreliacidal antibodies. *B. burgdorferi* OspC is another potential target for borreliacidal antibody-mediated immunity. This protein appears to have an epitope that is responsible for inducing borreliacidal antibodies, and is not conserved among the pathogenic *Borrelia* spp. Although the specific function of the OspC protein remains unknown, it has been suggested that OspC expression is required for infection of mammals, but not for infection of ticks. *Borrelia* express OspC shortly after the tick begins feeding, and must continue to express OspC in order to establish an infection in mammals. Therefore, the "window of effectiveness" of the OspC borreliacidal antibodies is increased significantly, compared to OspA borreliacidal antibodies.

Callister et al., (U.S. Pat. Nos. 6,210,676 and 6,464,985, incorporated by reference herein) have suggested employing an immunogenic polypeptide fragment of OspC, alone or in combination with an OspA polypeptide, to prepare a vaccine to protect humans and other mammals against Lyme disease. Livey et al. (U.S. Pat. No. 6,872,550, incorporated by reference herein) also proposed a vaccine for immunizing against Lyme disease prepared from a combination of recombinant OspA, OspB, and OspC proteins.

However, at least two obstacles need to be overcome before a successful vaccine can be created. First, there are over twenty OspC phylotypes, and it is unclear which ones should be included into a vaccine. Second, suitable epitopes for development of borreliacidal anti-OspC antibodies need to be determined.

Therefore, there remains a longstanding need in the art for an improved vaccine to protect mammals, and especially canines, from Lyme disease.

SUMMARY OF INVENTION

The instant invention addresses these and other needs by providing, in one aspect, an immunogenic composition comprising: a first protein comprising an amino acid sequence at least 95% identical to SEQ ID NO: 1 (MDPNTVSSFQVDSFLWHVRKRVADQELGDAPFLDRLRRDQKSLRGRGSTLG LDIETATRAGKQIVERILKEESDEALKMTMGKQNVSSLDEKNSVSVDLPGEMNV LVSKEKNKDGKYDLIATVDKLELKGTSDKNNGSGVLEGVKADKSKVKLTISDDL GQTTLEVFKEDGKTLVSKKVTSKDKSSTEEKFNEKGEVSEKIITRADGTRLEYT EIKSDGSGKAKEVLKSYVLEGTLTAEKTTLVVKEGTVTLSKNISKSGEVSVELND TDSSAATKKTAAWNSGTSTLTITVNSKKTKDLVFTKENTITVQQYDSNGTKLEG SAVEITKLDEIKNALK); and a second protein, comprising immunodominant epitopes of OspC phylotypes F and N.

In a set of embodiments, the second protein comprises a plurality of peptides at least 95% identical to immunodominant epitopes from loop 5 (loop peptide) and alpha helix 5 (helix peptide) of one or more OspC phylotypes I, H, C, M, and D, wherein further the loop peptides and the helix peptide from each phylotype are adjacent to each other and wherein the loop peptides and the helix peptides are arranged sequentially; and at least one of: a loop peptide and a helix peptide of OspC phylotype F adjacent to each other, or an amino acid sequence 95% identical to SEQ ID NO 32. In one set of embodiments, if said amino acid sequence 95% identical to SEQ ID NO: 32 is present, it is at the carboxy terminus of said second protein.

In one set of embodiments, the first protein is SEQ ID NO: 1. In another set of embodiments, the loop and helix peptides of phylotypes I, H, N, C, M, D and F are at least 95% identical to SEQ ID NOs: 4-17, respectively.

In another set of embodiments, the immunogenic composition may also comprise additional loop and helix peptides from one or more OspC phylotypes F, T, U, E, A, B, and K, which are, in some embodiments, identical to SEQ ID NOs 16-29, respectively.

In yet another set of embodiments, the immunogenic composition may further comprise at least one additional antigen protective against a microorganism that can cause disease in dogs. The microorganism may be selected from the group comprising canine distemper (CD) virus, canine adenovirus type 2 (CAV-2), canine parainfluenza (CPI) virus, canine parvovirus (CPV), canine coronavirus (CCV), canine herpesvirus, and rabies virus. Antigens from these pathogens for use in the vaccine compositions of the present invention can be in the form of a modified live viral preparation or an inactivated viral preparation. Other pathogens also include *Leptospira bratislava, Leptospira canicola, Leptospira grippotyphosa, Leptospira icterohaemorrhagiae, Leptospira pomona, Leptospira hardjobovis, Porphyromonas* spp., *Bacteriodes* spp., *Leishmania* spp., *Ehrlichia* spp., *Mycoplasma* ssp. and *Microsporum canis.*

In particular embodiments, the immunogenic composition comprises SEQ ID NO: 1 and either SEQ ID NO: 30 or SEQ ID NO: 31.

In another aspect, the instant invention provides a vaccine composition comprising the immunogenic composition as described above. The vaccine can also comprise an adjuvant and a pharmaceutically acceptable carrier. In different embodiments, adjuvants include, without limitations mineral salts, surface-active agents and microparticles, bacterial products, cytokines and hormones, carriers, oil-in-water emulsions and water-in-oil emulsions.

In yet another aspect, the invention also provides a method of preventing Lyme disease in a canine comprising administering to the canine in need thereof an immunologically effective dose of the vaccine composition.

BRIEF DESCRIPTION OF THE FIGURES

FIG. 1 illustrates neighbor joining tree of OspC types identified by cloning from skin biopsy samples taken from dogs.

FIG. 2 illustrates neighbor joining tree of OspC types identified by sequencing *Borrelia burgdorferi* clones isolated from skin biopsies taken from dogs.

FIGS. 3A and 3B illustrate chimeric sequences A12CF and A10CF (SEQ ID NO: 31 and 30, respectively), suitable as the second protein of the immunogenic composition described herein.

FIG. 4 illustrates protein sequence for OspC phylotype A strain B31 and other OspC phylotypes.

DETAILED DESCRIPTION OF PREFERRED EMBODIMENTS

For a better understanding of the instant application, the following non-limiting definitions are provided:

The term "at least 95% identical" includes all percentages of identity including and between 95% and 100%, for example, 96%, 97%, 98%, 99%, etc.

The term "alpha helix 5 region" or "helix 5 region" refers to amino acid sequence located between residues 160 and 200 of OspC phylotype A strain B31, and contains secondary structural elements including a portion of loop 6, alpha helix 5, and the unstructured C-terminal domain (Kumaran et al., 2001).

The term "conservative substitution" denotes the replacement of an amino acid residue by another biologically similar residue, or the replacement of a nucleotide in a nucleic acid sequence such that the encoded amino acid residue does not change or is another biologically similar residue. Examples of conservative substitution include the substitution of one hydrophobic residue such as isoleucine, valine, leucine or methionine for another hydrophobic residue, or the substitution of one polar residue for another polar residue, such as the substitution of arginine for lysine, glutamic for aspartic acid, or glutamine for asparagine, and the like. The term "conservative substitution" also includes the use of a substituted amino acid in place of an unsubstituted parent amino acid, provided that antibodies raised to the substituted polypeptide also immunoreact with the unsubstituted polypeptide.

The term "conservative variation" of a reference protein or a reference nucleic acid refers to a protein or a nucleic acid, respectively, which differs from the reference molecule by only conservative substitution(s).

The term "construct" preceded by a phylotype name (e.g., N-construct or I-construct) refers to an amino acid sequence comprising the loop peptide and the helix peptide.

The term "helix peptide" or "alpha helix peptide" of a certain phylotype of OspC refers to a peptide which is at least 95% identical to an immunodominant epitope from alpha helix 5 region of OspC protein of that phylotype. Thus, for example, helix peptide N refers to a peptide which is at least 95% identical to an immunodominant epitope from alpha helix 5 region of OspC phylotype N.

The term "immunodominant epitope" refers to an epitope on a molecule that induces a dominant, or intense, immune response when compared to other epitopes, including one or both B- and T-cell responses.

The term "linear epitope" refers to an epitope comprising a single, non-interrupted, contiguous chain of amino acids joined together by peptide bonds to form a peptide or polypeptide. Such an epitope can be described by its primary structure, i.e. the linear sequence of amino acids in the chain. Such an epitope, when expressed in a recombinant protein subunit of OspC, retains the ability to bind infection-induced antibodies in a manner similar to the binding of wild-type protein.

The term "loop peptide" of a certain phylotype of OspC refers to a peptide which is at least 95% identical to an immunodominant epitope from loop 5 region of OspC protein of that phylotype. Thus, for example, loop peptide N refers to a peptide which is at least 95% identical to an immunodominant epitope from loop 5 region of OspC phylotype N.

The term "loop 5 region" refers to amino acid sequence generally located between residues 131 and 159 of OspC phylotype A strain B31 and contains secondary structural elements, including a portion of alpha helix 3, loop 5 and alpha helix 4. See Kumaran et al., 2001. The sequence for OspC phylotype A strain B31 is provided in SEQ ID NO: 35 and in FIG. 4.

The term "therapeutically effective amount" as used herein means an amount of a microorganism, or a subunit antigen, or polypeptides, or polynucleotide molecules, and combinations thereof, sufficient to elicit an immune response in the subject to which it is administered. The immune response can comprise, without limitation, induction of cellular and/or humoral immunity.

The terms "vaccine" and "vaccine composition," as used herein, mean a composition which prevents or reduces an infection, or which prevents or reduces one or more signs or symptoms of infection. The protective effects of a vaccine composition against a pathogen are normally achieved by inducing in the subject an immune response, either a cell-mediated or a humoral immune response or a combination of both. Generally speaking, abolished or reduced incidences of infection, amelioration of the signs or symptoms, or accelerated elimination of the microorganism from the infected subjects are indicative of the protective effects of a vaccine composition.

In a broad aspect, the instant invention provides an immunogenic composition capable of inducing antibodies against OspA and OspC proteins of *Borrelia burgdorferi*. Thus, the composition will include two proteins: the first protein comprising an OspA or a fragment thereof, and a second protein, comprising an OspC protein or a fragment thereof. In some embodiments, the second protein is a chimeric protein comprising multiple fragments of OspC proteins of different phylotypes.

In some embodiments, the first protein comprises a fragment of OspA protein (SEQ ID NO: 2) (MGKQN-VSSLDEKNSVSVDLPGEMNVLVSKEKNKDGKYDLI-ATVDKLELKGTS DKNNGSGVLEGVKADKSKVKLTISDDLGQT-TLEVFKEDGKTLVSKKVTSKDKS STEEKFNEK-GEVSEKIITRADGTRLEYTEIKSDGSGKAKEVLKSYV-LEGTLTAET TLVVKEGTVTLSKNISKSGEVSVELNDTDSSAATKK-TAAWNSGTSTLTITVNSK KTKDLVFTKENTIT-VQQYDSNGTKLEGSAVEITKLDEIKNALK), which is immediately downstream of a viral protein, such as, for example, a fragment of the influenza virus NS1 protein, which is SEQ ID NO: 3 (MDPNTVSSFQVDSFL-WHVRKRVADQELGDAPFLDRLRRDQKSLRGRG-STLG LDIETATRAGKQIVERILKEESDEALKMT). An important requirement for the first protein is its ability to generate anti-OspA antibodies in a vaccinated animal. Thus, the full length sequence of the OspA fragment is not necessary, and neither is the 100% identity to SEQ ID NO: 2.

As noted elsewhere in the application, 95% sequence identity is likely to be sufficient to provide suitable level of antibody production. The differing amino acids can be conservative substitutions, and/or are located outside of immunodominant epitope(s) of the OspA fragment.

In other embodiments, shorter OspA fragments can be used. A person of ordinary skill in the art would know how to determine which OspA fragments contain immunodominant epitopes capable of generating borreliacidal antibodies.

The inventors have surprisingly found that the first protein comprising, from N- to C-terminus, a fragment of the influenza virus NS-1 protein, followed by OspA protein with its signal sequence removed, is particularly suitable for the immunogenic compositions of the instant invention.

Prior art studies are silent as to what phylotypes of OspC are prevalent in invasive Lyme disease in dogs. Most studies have been performed on human samples. Jones et al reports that the most prevalent phylotypes found in joint fluid of the human patients with arthritis are K and A, and typically, and phylotypes A, B, C, D, H, K, N were discovered. *Arthritis Rheum* 2009 60(7) 2174. Earnhart et al have discovered phylotypes A, B, I, K, C, D, N in blood and/or CSF samples *Infect Immun.* 2005 73(12): 7869. Other studies typically associated phylotypes A, B, I and K with invasive forms of Lyme disease in humans.

However, it was surprisingly discovered that in dogs, the most prevalent phylotype is OspC F, which was not previously associated with invasive form of Lyme disease, whether in humans or in dogs. Phylotype N, which is associated with invasive Lyme disease in humans, was also associated with invasive Lyme disease in dogs. Additionally, the inventors have discovered that phylotypes T and U, previously not associated with invasive Lyme disease in humans, may cause invasive Lyme disease in dogs.

According to some embodiments, the second protein contains immunodominant epitopes capable of generating immune response against different OspC protein phylotypes. More specifically, the second protein of the immunogenic composition claimed in the instant invention is a chimeric protein that comprises immunodominant epitopes of OspC phylotypes F and N. The immunodominant epitopes may be in the form of loop and/or helix peptides as discussed below, or they may be present within larger fragments of the target OspC protein. A suitable non-limiting example of such fragments is SEQ ID NO: 32 (NNSGKDGNTSANSADES-VKGPNLTEISKKITESNAVVLAVKEIETLLSSIDELAT KAIGQKIDANGLGVQANQNGSLLAGAYAIST-LITQKLSALNSEDLKEKVAKVKKC SEDFTNKLKNG-NAQLGLAAATDDNAKAAILKTNGTNDKGAKE-LKDLSDSVESLV KAAQVMLTNSVKELTSPVVAESPKKP), which is a fragment of OspC phylotype F protein.

Previous studies demonstrate that the inclusion of conserved region of OspC protein (i.e., conserved among different phylotypes) is important for generation of anti-borrelicidal antibody in mice and humans but not in dogs. See Lovrich et al, *Clin. and Vaccine Immunol.* May 2007, p. 635-637. Nevertheless, the inventors have surprisingly discovered that the addition of the longer fragment of one of the OspC phylotypes (e.g., phylotype F) is beneficial for the expression level and thus makes the manufacturing of the second protein more efficient.

Buckles et al demonstrated that loop 5 of OspC protein is surface exposed and may be a suitable target for generating borreliacidal antibodies. *Clin Vaccine Immunol.* 2006 October; 13(10):1162-5. See also WO09135118. However, considering that at least 21 phylotypes of OspC have been described (Seinost et al., *Infect Immun.* 1999 July; 67(7): 3518-24 1999), it remains to be determined what combination provides suitable protection against Lyme disease.

Thus, in some embodiments, the second protein comprises linear epitopes from loop 5 region (loop peptides) and helix 5 regions (helix 5 peptides) of OspC proteins of different phylotypes. Currently considered phylotypes are T, U, E, A, B, K, I, H, N, C, M, D and F. The second protein may thus comprise loop and helix peptides from 2-13 phylotypes of OspC, e.g., 2, 3, 4, 5, 6, 7, 8, 9, 10, 11, 12, 13 phylotypes. The order of the peptides is not crucial. In some embodiments, the loop peptides are interspaced with the helix peptides, and vice versa. In other words, the loop and helix peptides are arranged sequentially: in such embodiments, no two loop peptides should be present in the second protein without a helix peptide between them, and no two helix peptides should be present without a loop peptide between them.

A person of ordinary skill in the art would be aware how to determine immunodominant epitopes from the loop regions and helix regions of various OspC phylotypes. For example, sera from subjects infected with *Borrelia burgdorferi* of different phylotypes may be reacted with specific peptides from the loop regions and helix regions of the corresponding phylotypes, and the binding of the antibodies present in the sera to the loop peptides and/or helix peptides can be quantified (e.g., by ELISA, immunoblot, etc), thus providing clues as to which peptides contain immunodominant linear epitopes from a given OspC phylotype.

Similarly, the borreliacidal activity of the antibodies may be determined by methods well known in the art, e.g., generally, by co-incubating cultured *Borrelia burgdorferi* with the sera from subjects challenged with the immunodominant linear epitopes as described above, and quantification of living and dead *Borrelia.*

In some embodiments, the sequences for the loop peptides and helix peptides are as follows:

Loop peptide I is at least 95% identical to SEQ ID NO: 4 (AKLKGEHTDLGKEGVT);

Helix peptide I is at least 95% identical to SEQ ID NO: 5 (KGADELEKLFESVKNLSKAAKEMLTNSVKE);

Loop peptide H is at least 95% identical to SEQ ID NO: 6 (SEKFAGKLKNEHASLGKKDAT);

Helix peptide H is at least 95% identical to SEQ ID NO: 7 (KGAKELKDLSDSVESLVKA);

Loop peptide N is at least 95% identical to SEQ ID NO: 8 (SDDFTKKLQSSHAQLGVAGGATT);

Helix peptide N is at least 95% identical to SEQ ID NO: 9 (ADELEKLFKSVESLAKAAQDALANSVNELTS);

Loop peptide C is at least 95% identical to SEQ ID NO: 10 (KKLKEKHTDLGKKDAT);

Helix peptide C is at least 95% identical to SEQ ID NO: 11 (AAELEKLFESVENLAKAAKEMLSNS);

Loop peptide M is at least 95% identical to SEQ ID NO: 12 (NKAFTDKLKSSHAELGIANGAAT); Helix peptide M is at least 95% identical to SEQ ID NO: 13 (KGAQELE-KLFESVKNLSKAAQETLNNSVKE);

Loop peptide D is at least 95% identical to SEQ ID NO: 14 (SESFTKKLSDNQAELGIENAT);

Helix peptide D is at least 95% identical to SEQ ID NO: 15 (KGAEELVKLSESVAGLLKAAQAILANS-VKELTSPVVAESPKKP);

Loop peptide F is at least 95% identical to SEQ ID NO: 16 (SEDFTNKLKNGNAQLGLAAAT);

Helix peptide F is at least 95% identical to SEQ ID NO: 17 (KGAKELKDLSDSVESLVKAAQVMLTNS);

Loop peptide T is at least 95% identical to SEQ ID NO: 18 (STGFTNKLKSGHAELGPVGGNAT);

Helix peptide T is at least 95% identical to SEQ ID NO: 19 (KGAKELKDLSESVEALAKAAQAMLTNS);

Loop peptide U is at least 95% identical to SEQ ID NO: 20 (SEKFTKKLSESHADIGIQAAT);

Helix peptide U is at least 95% identical to SEQ ID NO: 21 (KGAEELDKLFKAVENLSK);

Loop peptide E is at least 95% identical to SEQ ID NO: 22 (STEFTNKLKSEHAVLGLDNLT);

Helix peptide E is at least 95% identical to SEQ ID NO: 23 (KGAAELEKLKAVENLSKAAQDTLKNAVKELTSPI-VAESPKKP);

Loop peptide A is at least 95% identical to SEQ ID NO: 24 (SETFTNKLKEKHTDLGKEGVT);

Helix peptide A is at least 95% identical to SEQ ID NO: 25 (KGAEELGKLFESVEVLSKAAKEMLANSVKELTS);

Loop peptide B is at least 95% identical to SEQ ID NO: 26 (SEEFSTKLKDNHAQLGIQGVT);

Helix peptide B is at least 95% identical to SEQ ID NO: 27 (KGVEELEKLSGSLESLS);

Loop peptide K is at least 95% identical to SEQ ID NO: 28 (SEDFTKKLEGEHAQLGIENVT); and Helix peptide K is at least 95% identical to SEQ ID NO: 29 (AAELEKLFKAVENLAKAAKEM).

In some embodiments, loop and helix peptides from the same phylotype are positioned together, i.e., adjacent to each other. For example, loop peptide from OspC phylotype A and a helix peptide from OspC phylotype A should not be separated by either the loop or the helix peptide from any other OspC phylotype.

Further, while in some embodiments, the loop and helix peptides from the same OspC phylotype are immediately adjacent to each other, in other embodiments, the loop peptide and the helix peptide may be separated by a linker sequence which does not affect the structure of the final protein. The properties of amino acids and their effects on protein structure are well known in the art and persons of ordinary skill in the art would be able to recognize which amino acids are suitable for the linkers.

As will be demonstrated in the Examples, the inventors have surprisingly found that F and N are the most prevalent OspC phylotypes associated with Lyme disease in dogs. The inventors have also found that the presence of loop and helix peptides from phylotypes I, H, N, C, M, D and F provides a very good level of protection against Lyme disease in dogs. While the order of the loop and helix peptides from different phylotypes is not crucial, in some embodiments, the second protein comprises, in N- to C-orientation, an I-construct, a H-construct, a N-construct, a C-construct, a M-construct, a D-construct, followed by an amino acid sequence which is at least 95% identical to a fragment of OspC phylotype F protein (e.g., SEQ ID NO: 32). Thus, in some embodiments, the second protein will comprise an amino acid sequence at least 95% (e.g., 96%, 97%, 98%, 99%, and preferably, 100%) identical to SEQ ID NO: 31 (A12CF).

In other embodiments, the loop and the helix peptides from phylotypes F, T, U, E, A, B, K are included within the second protein. In some embodiments, the second protein, thus, would comprise the following, in N- to C-orientation: a T-construct, a U-construct, a E-construct, an A-construct, a B-construct, a K-construct, the I-construct, the H-construct, the N-construct, the C-construct, the M-construct, and the D-construct. Optionally, the second protein can also comprise an F-construct, which is, in some embodiments, is upstream of the T-construct. Alternatively, or additionally, the second protein can contain the amino acid sequence which is at least 95% (e.g., 96%, 97%, 98%, 99%) identical to the fragment of OspC phylotype F protein (SEQ ID NO: 32).

Other suitable examples of the second protein, as well as methods of making and using same are provided in Application PCT/US2011/056854 (filed on Oct. 19, 2011, inventors R. Marconi and C. Earnhart).

In certain embodiments, the immunogenic composition would comprise SEQ ID NO: 1; and either one of SEQ ID NO: 30 or SEQ ID NO: 31.

The sequences described herein may be manufactured by methods well known in the art. The polypeptides may be produced by direct peptide synthesis using solid-phase techniques (see, e.g., Stewart et al. (1969) Solid-Phase Peptide Synthesis, WH Freeman Co, San Francisco; Merrifield J. (1963) *J Am Chem Soc* 85:2149-2154). Peptide synthesis may be performed using manual techniques or by automation. Automated synthesis may be achieved, for example, using Applied Biosystems 431A Peptide Synthesizer (Perkin Elmer, Foster City, Calif.), in accordance with the instructions provided by the manufacturer. For example, subsequences may be chemically synthesized separately and combined using chemical methods to provide full-length polypeptides or fragments thereof. Alternatively, such sequences may be ordered from any number of companies which specialize in production of polypeptides. Most commonly, polypeptides may be produced by expressing coding nucleic acids and recovering polypeptides, as described below.

For example, in embodiments where loop peptides and the helix peptides are 100% identical to the fragments of OspC proteins of the target phylotypes, the nucleic acid sequences of such loop and helix peptides are also known or easily accessible from publicly available databases, e.g., Genbank. If the selected loop/helix peptides are somewhat different from the naturally occurring fragments of OspC proteins, the encoding nucleic acid sequences can be easily designed using well known genetic code.

Many organisms display bias for use of particular codons to code for insertion of a particular amino acid in a growing peptide chain. Codon preference or codon bias, differences in codon usage between organisms, is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, since the majority of amino acids are encoded by multiple codons (methionine is the exception), the nucleic acid sequences can be tailored for optimal gene expression in a given organism based on codon optimization.

Methods for producing recombinant polypeptides are also included. One such method comprises introducing into a population of cells any nucleic acid as described above, which is operatively linked to a regulatory sequence effective to produce the encoded polypeptide, culturing the host cells (e.g., yeast, insect, mammalian cells, plant cells, etc) in a culture medium to express the polypeptide, and isolating the polypeptide from the cells or from the culture medium. The nucleic acid is introduced into such cells by any delivery method as is known in the art, including, e.g., transformation, transfection, injection, gene gun, passive uptake, etc. As one skilled in the art will recognize, the nucleic acid may be part of a vector, such as a recombinant expression vector, including a DNA plasmid vector, or any vector as known in the art.

Alternatively, cell-free prokaryotic or eukaryotic-based expression systems may be used.

In some embodiments, the nucleic acid sequence encoding the first and/or second protein, may further comprise a sequence encoding a polypeptide (the "fusion partner") that is fused to the first and/or second protein, thereby facilitating purification of the fusion protein. In certain embodiments of this aspect of the invention, the fusion partner is a hexahistidine peptide (SEQ ID NO: 47, HHHHHH), as provided in the pQE vector (Qiagen, Inc.), and described in Gentz et al., *Proc Natl Acad Sci USA* 86:821-824 (1989), or it may be the HA tag, which corresponds to an epitope derived from the influenza hemagglutinin protein (Wilson, I., et al., *Cell* 37:767, 1984). The polynucleotide may also contain noncoding 5' and 3' sequences, such as transcribed, non-translated sequences, splicing and polyadenylation signals, ribosome binding sites and sequences that stabilize mRNA.

The immunogenic compositions described herein are particularly suitable for preventing or diminishing the severity of symptoms of Lyme disease in dogs. Thus, in another aspect, the instant invention provides a vaccine, comprising the immunogenic composition according to any of the embodiments described above, and a suitable adjuvant.

The first and the second proteins of the immunogenic composition of the instant invention should be present in immunologically effective amount, i.e., in an amount sufficient to trigger the immune response in the dog. In some embodiments, the concentration of the first protein is between 1 and 100 ug/ml (e.g., 5, 10, 20, 30, 40, 50, 60, 70, 80, 90 ug/ml), and the concentration of the second protein is between 1 and 200 ug/ml (e.g., 5, 10, 20, 30, 40, 50, 60, 70, 80, 90, 100, 110, 120, 130, 140, 150, 160, 170, 180, 190 ug/ml). In some embodiments, the amount of the first protein is between about 10 and 50 ug/ml and the amount of the second protein is between 20 and 100 ug/ml.

Adjuvants suitable for use in accordance with the present invention include, but are not limited to several adjuvant classes such as; mineral salts, e.g., Alum, aluminum hydroxide, aluminum hydroxide gels (e.g., Rehydragel®), aluminum phosphate and calcium phosphate; surface-active agents and microparticles, e.g., nonionic block polymer surfactants, cholesterol, virosomes, saponins (e.g., Quil A, QS-21 and GPI-0100), proteosomes, immune stimulating complexes, cochleates, quarterinary amines (dimethyl diocatadecyl ammonium bromide (DDA)), pyridine, vitamin A, vitamin E; bacterial products such as the RIBI adjuvant system (Ribi Inc.), cell wall skeleton of *Mycobacterum phlei* (Detox®), muramyl dipeptides (MDP) and tripeptides (MTP), monophosphoryl lipid A, *Bacillus* Calmete-Guerin, heat labile *E. coli* enterotoxins, cholera toxin, trehalose dimycolate, CpG oligodeoxnucleotides; cytokines and hormones, e.g., interleukins (IL-1, IL-2, IL-6, IL-12, IL-15, IL-18), granulocyte-macrophage colony stimulating factor, dehydroepiandrosterone, 1,25-dihydroxy vitamin $D_3$; polyanions, e.g., dextran; polyacrylics (e.g., polymethylmethacrylate, Carbopol 934P); carriers e.g., tetanus toxid, diptheria toxoid, cholera toxin B subnuit, mutant heat labile enterotoxin of enterotoxigenic *E. coli* (rmLT), heat shock proteins; oil-in-water emulsions e.g., AMPHIGEN® (Hydronics, USA); and water-in-oil emulsions such as, e.g., Freund's complete and incomplete adjuvants. In other embodiments, SP oil may also be used. As used herein, the term "SP oil" designates an oil emulsion comprising a polyoxyethylene-polyoxypropylene block copolymer, squalane, polyoxyethylene sorbitan monooleate and a buffered salt solution. In general, the SP oil emulsion will comprise about 1 to 3% vol/vol of block copolymer, about 2 to 6% vol/vol of squalane, more particularly about 3 to 6% of squalane, and about 0.1 to 0.5% vol/vol of polyoxyethylene sorbitan monooleate, with the remainder being a buffered salt solution.

The vaccines described herein may be combination vaccines which include the immunogenic composition described above, in combination with at least one antigen from other canine pathogens, capable of inducing a protective immune response in dogs against disease caused by such other pathogens.

Such other pathogens include, but are not limited to, canine distemper (CD) virus, canine adenovirus type 2 (CAV-2), canine parainfluenza (CPI) virus, canine parvovirus (CPV), canine coronavirus (CCV), canine herpesvirus, and rabies virus. Antigens from these pathogens for use in the vaccine compositions of the present invention can be in the form of a modified live viral preparation, an inactivated viral preparation, or a subunit protein preparation. In other embodiments, a recombinant CDV (Canine Distemper Virus) may also be used. Methods of attenuating virulent strains of these viruses, and methods of making an inactivated viral preparation, are known in the art, and are described in, e.g., U.S. Pat. Nos. 4,567,042 and 4,567,043.

Other pathogens also include *Leptospira bratislava, Leptospira canicola, Leptospira grippotyphosa, Leptospira icterohaemorrhagiae, Leptospira pomona, Leptospira hardjobovis, Porphyromonas* spp., *Bacteriodes* spp., *Leishmania* spp., *Ehrlichia* spp., *Mycoplasma* ssp., *Anaplasma* spp. and *Microsporum canis*. Antigens from these pathogens for use in the vaccine compositions of the present invention can be in the form of an inactivated whole or partial cell preparation, using methods well-known in the art. For example, methods of making an inactivated whole or partial *Leptospira* cell preparation are known in the art and are described in, e.g., Yan, K-T, "Aspects of Immunity to *Leptospira* borgpetersenii serovar hardjo", PhD Thesis, Appendix 1,1996. Faculty of Agriculture and Food Science, The Queen's University of Belfast; Mackintosh et al., "The use of a hardjo-pomona vaccine to prevent leptospiruria in cattle exposed to natural challenge with *Leptospia interrogans* serovarhardjo", *New Zealand Vet. J.* 28:174-177, 1980; Bolin et. al., "Effect of vaccination with a pentavalent leptopsiral vaccine on *Leptospira* interrogans serovar hardjo type hardjo-boivs infection of pregnant cattle", *Am. J. Vet. Res.* 50:161-165, 1989.

In accordance with the present invention, vaccines can be administered to a dog of at least 6 weeks old, or at least 7 weeks old, or at least 8 or 9 weeks old. The administration can be done by any known routes, including the oral, intranasal, mucosal topical, transdermal, and parenteral (e.g., intravenous, intraperitoneal, intradermal, subcutaneous or intramuscular). Administration can also be achieved using needle-free delivery devices. Administration can also be achieved using a combination of routes, e.g., first administration using a parental route, and subsequent administration using a mucosal route. In some embodiments, routes of administration include subcutaneous and intramuscular administrations.

All publications cited in the specification, both patent publications and non-patent publications, are indicative of the level of skill of those skilled in the art to which this invention pertains. All these publications are herein fully incorporated by reference, to the same extent as if each individual publication were specifically and individually indicated as being incorporated by reference.

For a clearer understanding of the invention, the following examples are set forth below. These examples are merely illustrative, and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLES

Example 1

Determination of *B. Burgdorferi* OspC Phylotypes Associated with Lyme Disease in Dogs Adult *Ixodes scapularis* ticks were collected in southern Rhode Island by flagging. The percentage of ticks infected with *B. burgdorferi* was determined through direct fluorescent microscopy using standard methods and labeled anti-*B. burgdorferi* antibody.

All procedures were conducted in compliance with regulations of the Animal Welfare Act and the dogs were maintained in accordance with Farm Canine Husbandry Standard Operating Procedures. Fifteen purpose-bred dogs of both sexes (7 males, 8 females; 9 to 10 weeks of age; Marshall Bioresources) were assigned identification numbers and divided into four study groups designated as T01 (n=4), T02 (n=4), T03 (n=4) and T04 (n=3). The dogs were fitted with Elizabethan collars and housed in one-over-one condo style cages. One day prior to tick infestation serum was collected from each dog. Dogs in study groups T01, T02, T03 and T04 were infested with 0, 25, 50 or 75 adult *Ixodes scapularis* ticks, respectively, using secured infestation chambers placed on each side of the midthorax. The ticks were fed to repletion, removed and serum samples and skin biopsies were collected at 49 and 90 days (relative to the start of infestation). Seroconversion was assessed with the SNAP 4DX test (IDEXX). To cultivate spirochetes, a portion of each skin biopsy was placed in BSK-H media (6% rabbit serum; 37EC, 5% $CO_2$). Clonal populations were obtained from the cultures by sub-surface plating as previously described. Colonies were excised from the plates and placed in BSK-H media for cultivation.

DNA was extracted from skin biopsies using the Qiagen DNeasy Kit as instructed by the supplier. In addition, DNA was extracted from cultures of the clonal populations of *B. burgdorferi* as previously described. The ospC gene was PCR amplified using DNA extracted from tissues (100 ng) and from DNA obtained from boiled *B. burgdorferi* cell lysates (1:1 supernatant; GoTaq polymerase). All PCR was performed using standard conditions. A portion of each reaction was assessed by agarose gel electrophoresis and ethidium bromide staining. The remaining PCR products were excised from the gels (Qiagen Gel Extraction Kit; QIAGEN) and annealed with the pET46Kk/LIC vector (Novagen). The plasmids were propagated in *E. coli* NovaBlue cells (Novagen). Colonies were screened for the ospC gene by PCR. The templates for PCR were generated by boiling a portion of each ospC positive, *E. coli* colony. Portions of the colonies were also inoculated into LB media (2 ml), grown overnight, harvested by centrifugation and plasmid extracted using the Qiagen MiniPrep kit (QIAGEN). The primers used for PCR are as follows (5' to 3'):

```
OspC-F1
                              (SEQ ID NO: 33)
GACGACGACAAGATTGAATACATTAAGTGCAATATTAATGAC

OspC-R1
                              (SEQ ID NO: 34)
GAGGAGAAGCCCGGTTTACAAATTAATCTTATAATATTGATC

TTAATTAAGG
```

DNA sequencing was performed by Eurofins MWG Operon. Neighbor joining trees were generated using ClustalX 2.0.10 software in the multiple alignment mode with the default settings and a Gonnet matrix and visualized using N-J Plot version 2.2.

Results

Analysis of the Prevalence of *B. Burgdorferi* in Ticks Collected from Rhode Island.

Using direct fluorescent microscopy it was determined that ~50% of the *Ixodes scapularis* ticks field-collected in southern Rhode Island were infected with *B. burgdorferi*. This is consistent with previously reported tick infection rates in this area.

Infection of Dogs with *Borrelia burgdorferi* Through Tick Infestation.

At the start of this study, all dogs were confirmed to be sero-negative for through immunoblot analyses and through the use of the *B. burgdorferi* using the SNAP 4DX assay (IDEXX). To infect dogs with *B. burgdorferi* via the natural transmission route, field collected ticks were fed on dogs. Since the infection rate in the ticks was ~50% increasing numbers of ticks (0, 25, 50 or 75) were placed on the dogs. Serum samples were collected 49 days after tick infestation and immunological status evaluated. Of the dogs infested with ticks, 10 of 11 were sero-positive for *B. burgdorferi*. All negative controls dogs (not infested with ticks) were sero-negative. Total DNA was extracted from skin biopsies collected from each dog and tested for *B. burgdorferi* by PCR with ospC and flaB primer sets. All seropositive dogs yielded ospC and flaB amplicons of the predicted size. All seronegative dogs were PCR negative for both genes.

Analysis of OspC Diversity in Strains Found in Infected Dog Tissues.

To determine the ospC genotype of strains that persisted in the skin of dogs exposed to ticks, ospC was PCR amplified from DNA extracted from skin biopsies. The resulting amplicons were cloned into pET46 Ek/LIC and the plasmids propagated in *E. coli*. Plasmid was then isolated from no less than 5 separate *E. coli* colonies and the ospC sequences determined. Sequence alignment and dendogram construction (FIG. 1) demonstrated the persistence of strains producing several different ospC types in 6 of the 10 dogs (Table 1). Since multiple ticks were used to infect each dog this observation is not surprising. OspC types A, B, F, I and N were identified with types F and N being the most prevalent (5/10 and 7/10 dogs, respectively).

To further define the range of ospC genotypes present in the infected dogs, cultures from the skin biopsies were plated to yield clonal populations. By this approach, strains expressing ospC types that were not detected by PCR of biospy samples can be identified. Individual *B. burgdorferi* colonies were then tested for ospC by PCR (FIG. 2). Additional ospC types were identified in 3 of 6 dogs. Two of the identified OspC types, both of which originated from the same dog, had not been previously identified. These phyletic types were designated as DRI85a and DRI85e. Other ospC types identified by this approach included types E, F, H, I, N, U and T (Table 1). Collectively, in these analyses a total of 11 different OspC types were detected.

TABLE 1

OspC types from sequencing biopsies and clonal isolates per group and per individual dog.

| Study group | | OspC Types | |
|---|---|---|---|
| Group # | Dog ID | Biopsy | Culture |
| T01 | controls | negative | negative |
| T02 | DRI85 | A, N | U, DRI85a, DRI85e |
| | DRI63 | N | not analyzed |
| | DRI16 | A, N | E |
| | DRI03 | B, F, N | H, N |
| T03 | DRI09 | I, N | not analyzed |
| | DRI05 | F | E, U |
| | DRI41 | B, I, N | not analyzed |
| | DRI83 | F | E |
| T04 | DRI40 | F, N | E, I, F, T |
| | DRI73 | F | not analyzed |

In this study the inventors determined the ospC genotype of Lyme disease spirochete strains that successfully established infection and persisted in dogs. Field collected *Ixodes scapularis* ticks from Rhode Island were fed on laboratory dogs and the ospC genotype of strains present in skin after 49 days was determined. A total of 11 different OspC types were identified. OspC type F, which has not been previously detected in humans, was the most frequently detected OspC type (50% of infected dogs). Types B, N and U, which occur with very low frequency in humans were also detected. Two ospC types that have not been previously defined (DRI85a and DRI85e) were also recovered. The diversity observed in this study is consistent with earlier studies that demonstrated the maintenance of several ospC phyletic types within a local *B. burgdorferi* population. In that the ticks used in this study were collected from a single geographic region, it is possible that strains expressing other OspC types that are not well represented in Rhode Island are also competent to infect dogs. In spite of this caveat, this study is the first to demonstrate that OspC types not previously associated with human infection can efficiently infect dogs, thus facilitating the rational design of a new generation canine Lyme disease vaccine.

Example 2

Efficacy of Recombinant Chimeric *Borrelia burgdoferi* OspC/OspA Vaccines in Dogs Thirty dogs, all in good general health, were chosen for the study. Blood samples were collected prior to the initial vaccination. Dogs received one of the following vaccines, as described in Table 2: T01: PBS (control product); T02: ug/ml OspA+30 ug/ml A12CF (SEQ ID NO: 31); T03: 20 ug/ml OspA+30 ug/ml A10CF (SEQ ID NO: 30). (A12CF consists of epitopes from multiple OspC phylotypes, linked together to form a single polypeptide. A10CF also consists of epitopes from multiple OspC phylotypes; its design is similar to that of A12CF.) Dogs were vaccinated twice, at 8 and 11 weeks of age, and then challenged at 14 weeks of age. Following vaccination, dogs were observed for 20 minutes for reactions or abnormalities. Injection sites were observed on Days 1, 2, 3 and 22, 23, 24 for swelling, pain, heat, abscess, drainage, etc. Each dog was fitted with an Elizabethan [E] collar one day prior to placing the ticks, and the dogs were monitored for their ability to move, eat and drink with E-collars in place. Twenty to forty pairs (male, female) of *Ixodes scapularis* adult ticks, collected from the northeast USA, were placed along the dorsal midline of each dog, and allowed to feed until repletion for a period of 7 to 10 days. Serum samples and skin biopsies were collected at prescribed intervals, and assayed to monitor infection. Replete or unattached, non-viable ticks were collected and stored at 4° C. At the end of the challenge, remaining ticks were removed and stored, and dogs were treated with a topical acaricide according to label, followed by a second application 30 days later. Dogs were observed daily for overall physical appearance and behavior. Clinical observations were performed (lameness and ataxia); if either was observed, that dog's body temperature (tympanic) was measured/recorded daily, until the clinical signs subsided. Blood collections and skin biopsies were performed per protocol, other than deviations in scheduling/timing, based on receipt of ticks and subsequent infestation. Punch skin biopsies were taken near the general site of tick attachments on the dorsal cervical region, and timed to coincide with blood collections. Final biopsies were taken immediately after euthanasia, and prior to necropsy.

TABLE 2

Study Design

| | | | Study Days (±7 after Day 21) | | | | |
|---|---|---|---|---|---|---|---|
| Treatment | N | IVP/CP | Vaccination | Tick Infestation | Blood Collection | Biopsy | Necropsy |
| T01 | 10 | PBS | 0 and 21 | 106-117 | −1, 20, 100, 145, 176, 196 | 100, 146, 177, 197, 198 | 197, 198 |
| T02 | 10 | A12CF + OspA Rehydragel LV | | | | | |
| T03 | 10 | A10CF + OspA Rehydragel LV | | | | | |

Results

No reactions or abnormalities were observed in any dogs following vaccination, nor were any abnormalities at the injection site (swelling, pain, heat, abscess, drainage, etc.). Body temperatures, measured using a tympanic probe, did not show an appreciable or sustained elevation. Intermittent lameness occurred in two dogs vaccinated with A12CF+OspA (T02), and one dog in the non-vaccinated group (T01) was lame on Days 192-193. Ataxia was not observed in any dogs during the study. Abnormal health events, including pyoderma, bite wounds, abrasions, loose stools, otitis externa, etc., were observed in some dogs during the study, but none were attributed to the vaccines or vaccinations.

A serological response, indicative of active *Borrelia burgdoferi* infection, was observed on Day 146 in 8 of 10 control dogs (T01), and in one dog in T02. Nine control dogs (T01) were serologically positive on Day 177, and all dogs in T01 were positive at the study conclusion. In contrast, there was only one dog in each vaccinated group that was positive from Day 177 to the conclusion of the study.

The ticks used in the study were dual infected with *B. burgdoferi* and *Anaplasma*. The results of the serological assay indicate that ticks successfully transmitted *Anaplasma* to the dogs. This supports the specificity of the vaccine constructs (T02, T03) against *B. burgdoferi* only.

ELISA values, expressed as geometric mean titers to each of OspA and OspC, were significantly different when comparing T01 versus T02, and T01 versus T03, on all days, with the exception of the comparison of T01 vs. T02 for OspC on Day 146 (Table 3).

TABLE 3

ELISA Geometric Means OspA, OspC by Group, and by Phase

| | | Pre-challenge | | Post-challenge | | |
|---|---|---|---|---|---|---|
| Antigen | Treatment | Day 20 | Day 100 | Day 146 | Day 177 | Day 198 |
| OspA | T01 | 89.82[a] | 81.23[a] | 162.45[a] | 151.57[a] | 263.90[a] |
| | T02 A12CF + OspA | 1299.60[b] | 5571.52[b] | 3200.00[b] | 2599.21[b] | 1600.00[b] |
| | T03 A10CF + OspA | 1437.16[b] | 5198.41[b] | 3939.66[b] | 2262.74[b] | 1600.00[b] |
| OspC | T01 | 100.34[a] | 93.30[a] | 1392.88[a] | 1969.83[a] | 1714.84[a] |
| | T02 A12CF + OspA | 373.21[b] | 696.44[b] | 800.00[a,b] | 696.44[b] | 527.80[b] |
| | T03 A10CF + OspA | 335.91[b] | 606.29[b] | 565.69[b] | 565.69[b] | 492.46[b] |

[a],[b]values with different superscripts are significantly different P ≤ 0.10

Serum samples collected during the post-challenge phase from control dogs (T01) and dogs in T02 (A12CF+OspA) were assayed in an ELISA which is specific for live *B. burgdoferi* organisms. The geometric mean titers for T01 vs T02 were: at Day 146, 90 vs 6; Day 177, 116 vs 7; and Day 198, 87 vs 7. Thus, these results support the vaccine's protective effect against *B. burgdoferi.*

Skin punch biopsy samples were cultured for viable spirochetes. In group T01, 4 dogs on Day 146, and 5 dogs on Day 177, were culture positive. One dog in each of T02 and T03 had a spirochete-positive skin culture on Day 177. No positive culture was obtained from any group at the conclusion of the study.

Skin punch biopsies were also assessed by PCR, using flab- and ospC-specific primers, for the presence of *B. burgdoferi* on Day 146. Five dogs in T01 were positive for flab, while 3 were positive for ospC. No dogs in either T02 or T03 were positive for either PCR reaction.

Examinations of joints and skin sections microscopically demonstrated that vaccination with either the T02 or T03 vaccine protected against infection (data not shown). Vaccinated dogs had fewer changes in their joints and skin as is characteristic of Lyme disease. If such changes were present, they were less severe in vaccinated dogs when compared to tissues from non-vaccinated control dogs. There was a slight difference between the two vaccines (T02; T03), based on the number of dogs with lesions in their joints (6 for T02; 7 for T03). However, a definitive conclusion cannot be drawn as to which construct provided better protection.

In conclusion, both A12CF+OspA (T02) and A10CF+OspA (T03) were efficacious in protecting dogs against *Borrelia burgdoferi* infection as transmitted by *Ixodes scapularis ticks.*

The invention claimed is:

1. An immunogenic composition comprising:

A) a first protein comprising an amino acid sequence at least 95% identical to SEQ ID NO: 1; and B) a second protein, comprising immunodominant epitopes of OspC phylotypes F and N; wherein said composition is useful for preventing or reducing the pathological effects of infection with *Borrelia burgdorferi* in a canine, wherein said second protein comprises i) at least one of an amino acid sequence at least 95% identical to SEQ ID NO: 8 and an amino acid sequence at least 95% identical to SEQ ID NO: 9; and ii) an amino acid sequence 95% identical to SEQ ID NO: 32.

2. The immunogenic composition of claim 1, wherein the first protein comprises SEQ ID NO; 1.

3. The immunogenic composition of claim 1, wherein the second protein further comprises:

a plurality of peptides at least 95% identical to immunodominant epitopes from loop 5 region (loop peptide) and alpha helix 5 region (helix peptide) of OspC phylotype I, H, C, M, and D.

4. The immunogenic composition of claim 3 wherein:

Loop peptide I is SEQ ID NO: 4;

Helix peptide I is SEQ ID NO: 5;

Loop peptide H is SEQ ID NO: 6;

Helix peptide H is SEQ ID NO: 7;

Loop peptide C is SEQ ID NO: 10;

Helix peptide C is SEQ ID NO: 11;

Loop peptide M is SEQ ID NO: 12;

Helix peptide M is SEQ ID NO: 13;

Loop peptide D is SEQ ID NO: 14;

Helix peptide D is SEQ ID NO: 15.

5. The immunogenic composition of claim 1, wherein the amino acid sequence 95% identical to SEQ ID NO 32 is at the carboxy terminus of said second protein.

6. The immunogenic composition of claim 1, wherein the second protein comprises, in N- to C-orientation, an I-construct, a H-construct, a N-construct, a C-construct, a M-construct, a D-construct.

7. The immunogenic composition of claim 1, wherein the second protein further comprises a plurality of peptides 95% identical to immunodominant epitopes from loop 5 region (loop peptide) and alpha helix 5 region (helix peptide) of OspC phylotypes T, U, E.

8. , The immunogenic composition of claim 7, wherein the second protein comprises, in N- to C-orientation, a T-construct, a U-construct, an E-construct.

9. The immunogenic composition of claim 1, wherein the second protein further comprises a plurality of peptides 95% identical to immunodominant epitopes from loop 5 region (loop peptide) and alpha helix 5 region (helix peptide) of OspC phylotypes A, B, K.

10. The immunogenic composition of claim 9, wherein the second protein comprises, in N- to C-orientation, an A-construct, a B-construct, a K-construct.

11. The immunogenic composition of claim 1, wherein the second protein comprises, in N- to C-orientation, the T-construct, the U-construct, the E-construct, an A-construct, a B-construct, a K-construct.

12. The immunogenic composition of claim 11, wherein the second protein comprises, in N- to C-orientation, the T-construct, the U-construct, the E-construct, the A-construct, the B-construct, the K-construct, an I-construct, an H-construct, an N-construct, a C-construct, an M-construct, a D-construct.

13. The immunogenic composition according to claim 1, wherein the loop peptides and the helix peptide from each phylotype are adjacent to each other.

14. The immunogenic composition according to claim 3, wherein the loop peptides and the helix peptides for each phylotype are arranged sequentially.

15. The immunogenic composition of claim 3, wherein the loop peptide for each phylotype is upstream of the corresponding helix peptide for that phylotype.

16. The immunogenic composition according to claim 1, wherein a. the first protein is SEQ ID NO: 1; and b. the second protein is SEQ ID NO: 30.

17. The immunogenic composition according to claim 1, wherein a. the first protein is SEQ ID NO: 1; and b. the second protein is SEQ ID NO: 31.

18. The immunogenic composition of claim 1 further comprising at least one additional antigen preventing or reducing the pathological effects of infection with a microorganism that can cause disease in dogs.

19. The immunogenic composition of claim 18, wherein said microorganism is selected from the group consisting of canine distemper (CD) virus, canine adenovirus type 2 (CAV-2), canine parainfluenza (CPI) virus, canine parvovirus (CPV), canine coronavirus (CCV), canine herpesvirus, and rabies virus.

20. A vaccine composition comprising the immunogenic composition according to claim 17 and an adjuvant.

21. The vaccine composition of claim 20, wherein the adjuvant is selected from the group consisting of mineral salts, surface-active agents and microparticles, bacterial products, cytokines and hormones, carriers, oil-in-water emulsions and water-in-oil emulsions.

22. A method of preventing or reducing the pathological effects of infection with *Borrelia burgdorferi* in a canine comprising administering the canine in need thereof an immunologically effective dose of the vaccine composition according to any one of claims 20 and 21.

23. A method of preventing or reducing the pathological effects of infection with *Borrelia burgdorferi* in a canine comprising administering the canine in need thereof an immunologically effective dose of the immunogenic composition according to any one of claims 1, 2, 3, 4, 5, 17.

* * * * *

SEQUENCE LISTING

```
<160> NUMBER OF SEQ ID NOS: 47

<210> SEQ ID NO 1
<211> LENGTH: 338
<212> TYPE: PRT
<213> ORGANISM: Artificial Sequence
<220> FEATURE:
<223> OTHER INFORMATION: chimeric protein

<400> SEQUENCE: 1

Met Asp Pro Asn Thr Val Ser Ser Phe Gln Val Asp Ser Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Gly Lys Gln Asn Val Ser Ser Leu Asp Glu Lys Asn Ser Val Ser
                85                  90                  95

Val Asp Leu Pro Gly Glu Met Asn Val Leu Val Ser Lys Glu Lys Asn
            100                 105                 110

Lys Asp Gly Lys Tyr Asp Leu Ile Ala Thr Val Asp Lys Leu Glu Leu
        115                 120                 125
```

```
Lys Gly Thr Ser Asp Lys Asn Asn Gly Ser Gly Val Leu Glu Gly Val
    130                 135                 140

Lys Ala Asp Lys Ser Lys Val Lys Leu Thr Ile Ser Asp Asp Leu Gly
145                 150                 155                 160

Gln Thr Thr Leu Glu Val Phe Lys Glu Asp Gly Lys Thr Leu Val Ser
                165                 170                 175

Lys Lys Val Thr Ser Lys Asp Lys Ser Ser Thr Glu Glu Lys Phe Asn
            180                 185                 190

Glu Lys Gly Glu Val Ser Glu Lys Ile Ile Thr Arg Ala Asp Gly Thr
        195                 200                 205

Arg Leu Glu Tyr Thr Glu Ile Lys Ser Asp Gly Ser Gly Lys Ala Lys
    210                 215                 220

Glu Val Leu Lys Ser Tyr Val Leu Glu Gly Thr Leu Thr Ala Glu Lys
225                 230                 235                 240

Thr Thr Leu Val Val Lys Glu Gly Thr Val Thr Leu Ser Lys Asn Ile
                245                 250                 255

Ser Lys Ser Gly Glu Val Ser Val Glu Leu Asn Asp Thr Asp Ser Ser
            260                 265                 270

Ala Ala Thr Lys Lys Thr Ala Ala Trp Asn Ser Gly Thr Ser Thr Leu
        275                 280                 285

Thr Ile Thr Val Asn Ser Lys Lys Thr Lys Asp Leu Val Phe Thr Lys
    290                 295                 300

Glu Asn Thr Ile Thr Val Gln Gln Tyr Asp Ser Asn Gly Thr Lys Leu
305                 310                 315                 320

Glu Gly Ser Ala Val Glu Ile Thr Lys Leu Asp Glu Ile Lys Asn Ala
                325                 330                 335

Leu Lys


<210> SEQ ID NO 2
<211> LENGTH: 257
<212> TYPE: PRT
<213> ORGANISM: Artificial Sequence
<220> FEATURE:
<223> OTHER INFORMATION: OspA protein fragment

<400> SEQUENCE: 2

Met Gly Lys Gln Asn Val Ser Ser Leu Asp Glu Lys Asn Ser Val Ser
1               5                   10                  15

Val Asp Leu Pro Gly Glu Met Asn Val Leu Val Ser Lys Glu Lys Asn
            20                  25                  30

Lys Asp Gly Lys Tyr Asp Leu Ile Ala Thr Val Asp Lys Leu Glu Leu
        35                  40                  45

Lys Gly Thr Ser Asp Lys Asn Asn Gly Ser Gly Val Leu Glu Gly Val
    50                  55                  60

Lys Ala Asp Lys Ser Lys Val Lys Leu Thr Ile Ser Asp Asp Leu Gly
65                  70                  75                  80

Gln Thr Thr Leu Glu Val Phe Lys Glu Asp Gly Lys Thr Leu Val Ser
                85                  90                  95

Lys Lys Val Thr Ser Lys Asp Lys Ser Ser Thr Glu Glu Lys Phe Asn
            100                 105                 110

Glu Lys Gly Glu Val Ser Glu Lys Ile Ile Thr Arg Ala Asp Gly Thr
        115                 120                 125

Arg Leu Glu Tyr Thr Glu Ile Lys Ser Asp Gly Ser Gly Lys Ala Lys
    130                 135                 140
```

-continued

Glu Val Leu Lys Ser Tyr Val Leu Glu Gly Thr Leu Thr Ala Glu Thr
145 150 155 160

Thr Leu Val Val Lys Glu Gly Thr Val Thr Leu Ser Lys Asn Ile Ser
165 170 175

Lys Ser Gly Glu Val Ser Val Glu Leu Asn Asp Thr Asp Ser Ser Ala
180 185 190

Ala Thr Lys Lys Thr Ala Ala Trp Asn Ser Gly Thr Ser Thr Leu Thr
195 200 205

Ile Thr Val Asn Ser Lys Lys Thr Lys Asp Leu Val Phe Thr Lys Glu
210 215 220

Asn Thr Ile Thr Val Gln Gln Tyr Asp Ser Asn Gly Thr Lys Leu Glu
225 230 235 240

Gly Ser Ala Val Glu Ile Thr Lys Leu Asp Glu Ile Lys Asn Ala Leu
245 250 255

Lys

<210> SEQ ID NO 3
<211> LENGTH: 80
<212> TYPE: PRT
<213> ORGANISM: Artificial Sequence
<220> FEATURE:
<223> OTHER INFORMATION: influenza virus NS1 protein fragment

<400> SEQUENCE: 3

Met Asp Pro Asn Thr Val Ser Ser Phe Gln Val Asp Ser Phe Leu Trp
1 5 10 15

His Val Arg Lys Arg Val Ala Asp Gln Glu Leu Gly Asp Ala Pro Phe
20 25 30

Leu Asp Arg Leu Arg Arg Asp Gln Lys Ser Leu Arg Gly Arg Gly Ser
35 40 45

Thr Leu Gly Leu Asp Ile Glu Thr Ala Thr Arg Ala Gly Lys Gln Ile
50 55 60

Val Glu Arg Ile Leu Lys Glu Glu Ser Asp Glu Ala Leu Lys Met Thr
65 70 75 80

<210> SEQ ID NO 4
<211> LENGTH: 16
<212> TYPE: PRT
<213> ORGANISM: Artificial Sequence
<220> FEATURE:
<223> OTHER INFORMATION: Loop peptide I

<400> SEQUENCE: 4

Ala Lys Leu Lys Gly Glu His Thr Asp Leu Gly Lys Glu Gly Val Thr
1 5 10 15

<210> SEQ ID NO 5
<211> LENGTH: 30
<212> TYPE: PRT
<213> ORGANISM: Artificial Sequence
<220> FEATURE:
<223> OTHER INFORMATION: Helix peptide I

<400> SEQUENCE: 5

Lys Gly Ala Asp Glu Leu Glu Lys Leu Phe Glu Ser Val Lys Asn Leu
1 5 10 15

Ser Lys Ala Ala Lys Glu Met Leu Thr Asn Ser Val Lys Glu
20 25 30

<210> SEQ ID NO 6

-continued

<211> LENGTH: 21
<212> TYPE: PRT
<213> ORGANISM: Artificial Sequence
<220> FEATURE:
<223> OTHER INFORMATION: Loop peptide H

<400> SEQUENCE: 6

```
Ser Glu Lys Phe Ala Gly Lys Leu Lys Asn Glu His Ala Ser Leu Gly
1               5                   10                  15

Lys Lys Asp Ala Thr
            20
```

<210> SEQ ID NO 7
<211> LENGTH: 19
<212> TYPE: PRT
<213> ORGANISM: Artificial Sequence
<220> FEATURE:
<223> OTHER INFORMATION: Helix peptide H

<400> SEQUENCE: 7

```
Lys Gly Ala Lys Glu Leu Lys Asp Leu Ser Asp Ser Val Glu Ser Leu
1               5                   10                  15

Val Lys Ala
```

<210> SEQ ID NO 8
<211> LENGTH: 23
<212> TYPE: PRT
<213> ORGANISM: Artificial Sequence
<220> FEATURE:
<223> OTHER INFORMATION: Loop peptide N

<400> SEQUENCE: 8

```
Ser Asp Asp Phe Thr Lys Lys Leu Gln Ser Ser His Ala Gln Leu Gly
1               5                   10                  15

Val Ala Gly Gly Ala Thr Thr
            20
```

<210> SEQ ID NO 9
<211> LENGTH: 31
<212> TYPE: PRT
<213> ORGANISM: Artificial Sequence
<220> FEATURE:
<223> OTHER INFORMATION: Helix peptide N

<400> SEQUENCE: 9

```
Ala Asp Glu Leu Glu Lys Leu Phe Lys Ser Val Glu Ser Leu Ala Lys
1               5                   10                  15

Ala Ala Gln Asp Ala Leu Ala Asn Ser Val Asn Glu Leu Thr Ser
            20                  25                  30
```

<210> SEQ ID NO 10
<211> LENGTH: 16
<212> TYPE: PRT
<213> ORGANISM: Artificial Sequence
<220> FEATURE:
<223> OTHER INFORMATION: Loop peptide C

<400> SEQUENCE: 10

```
Lys Lys Leu Lys Glu Lys His Thr Asp Leu Gly Lys Lys Asp Ala Thr
1               5                   10                  15
```

<210> SEQ ID NO 11
<211> LENGTH: 25
<212> TYPE: PRT
<213> ORGANISM: Artificial Sequence
<220> FEATURE:
<223> OTHER INFORMATION: Helix peptide C

<400> SEQUENCE: 11

```
Ala Ala Glu Leu Glu Lys Leu Phe Glu Ser Val Glu Asn Leu Ala Lys
1               5                   10                  15

Ala Ala Lys Glu Met Leu Ser Asn Ser
            20                  25
```

<210> SEQ ID NO 12
<211> LENGTH: 23
<212> TYPE: PRT
<213> ORGANISM: Artificial Sequence
<220> FEATURE:
<223> OTHER INFORMATION: Loop peptide M

<400> SEQUENCE: 12

```
Asn Lys Ala Phe Thr Asp Lys Leu Lys Ser Ser His Ala Glu Leu Gly
1               5                   10                  15

Ile Ala Asn Gly Ala Ala Thr
            20
```

<210> SEQ ID NO 13
<211> LENGTH: 30
<212> TYPE: PRT
<213> ORGANISM: Artificial Sequence
<220> FEATURE:
<223> OTHER INFORMATION: Helix peptide M

<400> SEQUENCE: 13

```
Lys Gly Ala Gln Glu Leu Glu Lys Leu Phe Glu Ser Val Lys Asn Leu
1               5                   10                  15

Ser Lys Ala Ala Gln Glu Thr Leu Asn Asn Ser Val Lys Glu
            20                  25                  30
```

<210> SEQ ID NO 14
<211> LENGTH: 21
<212> TYPE: PRT
<213> ORGANISM: Artificial Sequence
<220> FEATURE:
<223> OTHER INFORMATION: Loop peptide D

<400> SEQUENCE: 14

```
Ser Glu Ser Phe Thr Lys Lys Leu Ser Asp Asn Gln Ala Glu Leu Gly
1               5                   10                  15

Ile Glu Asn Ala Thr
            20
```

<210> SEQ ID NO 15
<211> LENGTH: 43
<212> TYPE: PRT
<213> ORGANISM: Artificial Sequence
<220> FEATURE:
<223> OTHER INFORMATION: Helix peptide D

<400> SEQUENCE: 15

```
Lys Gly Ala Glu Glu Leu Val Lys Leu Ser Glu Ser Val Ala Gly Leu
1               5                   10                  15

Leu Lys Ala Ala Gln Ala Ile Leu Ala Asn Ser Val Lys Glu Leu Thr
            20                  25                  30

Ser Pro Val Val Ala Glu Ser Pro Lys Lys Pro
        35                  40
```

-continued

<210> SEQ ID NO 16
<211> LENGTH: 21
<212> TYPE: PRT
<213> ORGANISM: Artificial Sequence
<220> FEATURE:
<223> OTHER INFORMATION: Loop peptide F

<400> SEQUENCE: 16

```
Ser Glu Asp Phe Thr Asn Lys Leu Lys Asn Gly Asn Ala Gln Leu Gly
1               5                   10                  15

Leu Ala Ala Ala Thr
            20
```

<210> SEQ ID NO 17
<211> LENGTH: 27
<212> TYPE: PRT
<213> ORGANISM: Artificial Sequence
<220> FEATURE:
<223> OTHER INFORMATION: Helix peptide F

<400> SEQUENCE: 17

```
Lys Gly Ala Lys Glu Leu Lys Asp Leu Ser Asp Ser Val Glu Ser Leu
1               5                   10                  15

Val Lys Ala Ala Gln Val Met Leu Thr Asn Ser
            20                  25
```

<210> SEQ ID NO 18
<211> LENGTH: 23
<212> TYPE: PRT
<213> ORGANISM: Artificial Sequence
<220> FEATURE:
<223> OTHER INFORMATION: Loop peptide T

<400> SEQUENCE: 18

```
Ser Thr Gly Phe Thr Asn Lys Leu Lys Ser Gly His Ala Glu Leu Gly
1               5                   10                  15

Pro Val Gly Gly Asn Ala Thr
            20
```

<210> SEQ ID NO 19
<211> LENGTH: 27
<212> TYPE: PRT
<213> ORGANISM: Artificial Sequence
<220> FEATURE:
<223> OTHER INFORMATION: Helix peptide T

<400> SEQUENCE: 19

```
Lys Gly Ala Lys Glu Leu Lys Asp Leu Ser Glu Ser Val Glu Ala Leu
1               5                   10                  15

Ala Lys Ala Ala Gln Ala Met Leu Thr Asn Ser
            20                  25
```

<210> SEQ ID NO 20
<211> LENGTH: 21
<212> TYPE: PRT
<213> ORGANISM: Artificial Sequence
<220> FEATURE:
<223> OTHER INFORMATION: Loop peptide U

<400> SEQUENCE: 20

```
Ser Glu Lys Phe Thr Lys Lys Leu Ser Glu Ser His Ala Asp Ile Gly
1               5                   10                  15

Ile Gln Ala Ala Thr
            20
```

<210> SEQ ID NO 21
<211> LENGTH: 18
<212> TYPE: PRT
<213> ORGANISM: Artificial Sequence
<220> FEATURE:
<223> OTHER INFORMATION: Helix peptide U

<400> SEQUENCE: 21

```
Lys Gly Ala Glu Glu Leu Asp Lys Leu Phe Lys Ala Val Glu Asn Leu
1               5                   10                  15

Ser Lys
```

<210> SEQ ID NO 22
<211> LENGTH: 21
<212> TYPE: PRT
<213> ORGANISM: Artificial Sequence
<220> FEATURE:
<223> OTHER INFORMATION: Loop peptide E

<400> SEQUENCE: 22

```
Ser Thr Glu Phe Thr Asn Lys Leu Lys Ser Glu His Ala Val Leu Gly
1               5                   10                  15

Leu Asp Asn Leu Thr
            20
```

<210> SEQ ID NO 23
<211> LENGTH: 42
<212> TYPE: PRT
<213> ORGANISM: Artificial Sequence
<220> FEATURE:
<223> OTHER INFORMATION: Helix peptide E

<400> SEQUENCE: 23

```
Lys Gly Ala Ala Glu Leu Glu Lys Leu Lys Ala Val Glu Asn Leu Ser
1               5                   10                  15

Lys Ala Ala Gln Asp Thr Leu Lys Asn Ala Val Lys Glu Leu Thr Ser
            20                  25                  30

Pro Ile Val Ala Glu Ser Pro Lys Lys Pro
        35                  40
```

<210> SEQ ID NO 24
<211> LENGTH: 21
<212> TYPE: PRT
<213> ORGANISM: Artificial Sequence
<220> FEATURE:
<223> OTHER INFORMATION: Loop peptide A

<400> SEQUENCE: 24

```
Ser Glu Thr Phe Thr Asn Lys Leu Lys Glu Lys His Thr Asp Leu Gly
1               5                   10                  15

Lys Glu Gly Val Thr
            20
```

<210> SEQ ID NO 25
<211> LENGTH: 33
<212> TYPE: PRT
<213> ORGANISM: Artificial Sequence
<220> FEATURE:
<223> OTHER INFORMATION: Helix peptide A

<400> SEQUENCE: 25

```
Lys Gly Ala Glu Glu Leu Gly Lys Leu Phe Glu Ser Val Glu Val Leu
1               5                   10                  15
```

```
Ser Lys Ala Ala Lys Glu Met Leu Ala Asn Ser Val Lys Glu Leu Thr
            20                  25                  30

Ser


<210> SEQ ID NO 26
<211> LENGTH: 21
<212> TYPE: PRT
<213> ORGANISM: Artificial Sequence
<220> FEATURE:
<223> OTHER INFORMATION: Loop peptide B

<400> SEQUENCE: 26

Ser Glu Glu Phe Ser Thr Lys Leu Lys Asp Asn His Ala Gln Leu Gly
1               5                   10                  15

Ile Gln Gly Val Thr
            20


<210> SEQ ID NO 27
<211> LENGTH: 17
<212> TYPE: PRT
<213> ORGANISM: Artificial Sequence
<220> FEATURE:
<223> OTHER INFORMATION: Helix peptide B

<400> SEQUENCE: 27

Lys Gly Val Glu Glu Leu Glu Lys Leu Ser Gly Ser Leu Glu Ser Leu
1               5                   10                  15

Ser


<210> SEQ ID NO 28
<211> LENGTH: 21
<212> TYPE: PRT
<213> ORGANISM: Artificial Sequence
<220> FEATURE:
<223> OTHER INFORMATION: Loop peptide K

<400> SEQUENCE: 28

Ser Glu Asp Phe Thr Lys Lys Leu Glu Gly Glu His Ala Gln Leu Gly
1               5                   10                  15

Ile Glu Asn Val Thr
            20


<210> SEQ ID NO 29
<211> LENGTH: 21
<212> TYPE: PRT
<213> ORGANISM: Artificial Sequence
<220> FEATURE:
<223> OTHER INFORMATION: Helix peptide K

<400> SEQUENCE: 29

Ala Ala Glu Leu Glu Lys Leu Phe Lys Ala Val Glu Asn Leu Ala Lys
1               5                   10                  15

Ala Ala Lys Glu Met
            20


<210> SEQ ID NO 30
<211> LENGTH: 823
<212> TYPE: PRT
<213> ORGANISM: Artificial Sequence
<220> FEATURE:
<223> OTHER INFORMATION: chimeric sequence

<400> SEQUENCE: 30

Ser Glu Asp Phe Thr Asn Lys Leu Lys Asn Gly Asn Ala Gln Leu Gly
```

-continued

```
1               5                   10                  15

Leu Ala Ala Ala Thr Lys Gly Ala Lys Glu Leu Lys Asp Leu Ser Asp
            20                  25                  30

Ser Val Glu Ser Leu Val Lys Ala Ala Gln Val Met Leu Thr Asn Ser
        35                  40                  45

Ser Thr Gly Phe Thr Asn Lys Leu Lys Ser Gly His Ala Glu Leu Gly
    50                  55                  60

Pro Val Gly Gly Asn Ala Thr Lys Gly Ala Lys Glu Leu Lys Asp Leu
65                  70                  75                  80

Ser Glu Ser Val Glu Ala Leu Ala Lys Ala Ala Gln Ala Met Leu Thr
                85                  90                  95

Asn Ser Ser Glu Lys Phe Thr Lys Lys Leu Ser Glu Ser His Ala Asp
            100                 105                 110

Ile Gly Ile Gln Ala Ala Thr Lys Gly Ala Glu Glu Leu Asp Lys Leu
        115                 120                 125

Phe Lys Ala Val Glu Asn Leu Ser Lys Ser Thr Glu Phe Thr Asn Lys
    130                 135                 140

Leu Lys Ser Glu His Ala Val Leu Gly Leu Asp Asn Leu Thr Lys Gly
145                 150                 155                 160

Ala Ala Glu Leu Glu Lys Leu Phe Lys Ala Val Glu Asn Leu Ser Lys
                165                 170                 175

Ala Ala Gln Asp Thr Leu Lys Asn Ala Val Lys Glu Leu Thr Ser Pro
            180                 185                 190

Ile Val Ala Glu Ser Pro Lys Lys Pro Ser Glu Thr Phe Thr Asn Lys
        195                 200                 205

Leu Lys Glu Lys His Thr Asp Leu Gly Lys Glu Gly Val Thr Lys Gly
    210                 215                 220

Ala Glu Glu Leu Gly Lys Leu Phe Glu Ser Val Glu Val Leu Ser Lys
225                 230                 235                 240

Ala Ala Lys Glu Met Leu Ala Asn Ser Val Lys Glu Leu Thr Ser Ser
                245                 250                 255

Glu Glu Phe Ser Thr Lys Leu Lys Asp Asn His Ala Gln Leu Gly Ile
            260                 265                 270

Gln Gly Val Thr Lys Gly Val Glu Glu Leu Glu Lys Leu Ser Gly Ser
        275                 280                 285

Leu Glu Ser Leu Ser Ser Glu Asp Phe Thr Lys Lys Leu Glu Gly Glu
    290                 295                 300

His Ala Gln Leu Gly Ile Glu Asn Val Thr Ala Ala Glu Leu Glu Lys
305                 310                 315                 320

Leu Phe Lys Ala Val Glu Asn Leu Ala Lys Ala Ala Lys Glu Met Ala
                325                 330                 335

Lys Leu Lys Gly Glu His Thr Asp Leu Gly Lys Glu Gly Val Thr Lys
            340                 345                 350

Gly Ala Asp Glu Leu Glu Lys Leu Phe Glu Ser Val Lys Asn Leu Ser
        355                 360                 365

Lys Ala Ala Lys Glu Met Leu Thr Asn Ser Val Lys Glu Ser Glu Lys
    370                 375                 380

Phe Ala Gly Lys Leu Lys Asn Glu His Ala Ser Leu Gly Lys Lys Asp
385                 390                 395                 400

Ala Thr Lys Gly Ala Lys Glu Leu Lys Asp Leu Ser Asp Ser Val Glu
                405                 410                 415

Ser Leu Val Lys Ala Ser Asp Asp Phe Thr Lys Lys Leu Gln Ser Ser
            420                 425                 430
```

-continued

```
His Ala Gln Leu Gly Val Ala Gly Gly Ala Thr Thr Ala Asp Glu Leu
        435                 440                 445

Glu Lys Leu Phe Lys Ser Val Glu Ser Leu Ala Lys Ala Ala Gln Asp
    450                 455                 460

Ala Leu Ala Asn Ser Val Asn Glu Leu Thr Ser Lys Lys Leu Lys Glu
465                 470                 475                 480

Lys His Thr Asp Leu Gly Lys Lys Asp Ala Thr Ala Ala Glu Leu Glu
                485                 490                 495

Lys Leu Phe Glu Ser Val Glu Asn Leu Ala Lys Ala Ala Lys Glu Met
            500                 505                 510

Leu Ser Asn Ser Asn Lys Ala Phe Thr Asp Lys Leu Lys Ser Ser His
        515                 520                 525

Ala Glu Leu Gly Ile Ala Asn Gly Ala Ala Thr Lys Gly Ala Gln Glu
    530                 535                 540

Leu Glu Lys Leu Phe Glu Ser Val Lys Asn Leu Ser Lys Ala Ala Gln
545                 550                 555                 560

Glu Thr Leu Asn Asn Ser Val Lys Glu Ser Glu Ser Phe Thr Lys Lys
                565                 570                 575

Leu Ser Asp Asn Gln Ala Glu Leu Gly Ile Glu Asn Ala Thr Lys Gly
            580                 585                 590

Ala Glu Glu Leu Val Lys Leu Ser Glu Ser Val Ala Gly Leu Leu Lys
        595                 600                 605

Ala Ala Gln Ala Ile Leu Ala Asn Ser Val Lys Glu Leu Thr Ser Pro
    610                 615                 620

Val Val Ala Glu Ser Pro Lys Lys Pro Asn Asn Ser Gly Lys Asp Gly
625                 630                 635                 640

Asn Thr Ser Ala Asn Ser Ala Asp Glu Ser Val Lys Gly Pro Asn Leu
                645                 650                 655

Thr Glu Ile Ser Lys Lys Ile Thr Glu Ser Asn Ala Val Val Leu Ala
            660                 665                 670

Val Lys Glu Ile Glu Thr Leu Leu Ser Ser Ile Asp Glu Leu Ala Thr
        675                 680                 685

Lys Ala Ile Gly Gln Lys Ile Asp Ala Asn Gly Leu Gly Val Gln Ala
    690                 695                 700

Asn Gln Asn Gly Ser Leu Leu Ala Gly Ala Tyr Ala Ile Ser Thr Leu
705                 710                 715                 720

Ile Thr Gln Lys Leu Ser Ala Leu Asn Ser Glu Asp Leu Lys Glu Lys
                725                 730                 735

Val Ala Lys Val Lys Lys Cys Ser Glu Asp Phe Thr Asn Lys Leu Lys
            740                 745                 750

Asn Gly Asn Ala Gln Leu Gly Leu Ala Ala Ala Thr Asp Asp Asn Ala
        755                 760                 765

Lys Ala Ala Ile Leu Lys Thr Asn Gly Thr Asn Asp Lys Gly Ala Lys
    770                 775                 780

Glu Leu Lys Asp Leu Ser Asp Ser Val Glu Ser Leu Val Lys Ala Ala
785                 790                 795                 800

Gln Val Met Leu Thr Asn Ser Val Lys Glu Leu Thr Ser Pro Val Val
                805                 810                 815

Ala Glu Ser Pro Lys Lys Pro
            820
```

<210> SEQ ID NO 31
<211> LENGTH: 488

-continued

<212> TYPE: PRT
<213> ORGANISM: Artificial Sequence
<220> FEATURE:
<223> OTHER INFORMATION: chimeric sequence
<220> FEATURE:
<221> NAME/KEY: HELIX
<222> LOCATION: (17)..(46)
<223> OTHER INFORMATION: hxI
<220> FEATURE:
<221> NAME/KEY: HELIX
<222> LOCATION: (68)..(76)
<223> OTHER INFORMATION: hxH
<220> FEATURE:
<221> NAME/KEY: HELIX
<222> LOCATION: (100)..(130)
<223> OTHER INFORMATION: hxN
<220> FEATURE:
<221> NAME/KEY: HELIX
<222> LOCATION: (147)..(171)
<223> OTHER INFORMATION: hxC
<220> FEATURE:
<221> NAME/KEY: HELIX
<222> LOCATION: (195)..(224)
<223> OTHER INFORMATION: hxM
<220> FEATURE:
<221> NAME/KEY: HELIX
<222> LOCATION: (246)..(288)
<223> OTHER INFORMATION: hxD

<400> SEQUENCE: 31

```
Ala Lys Leu Lys Gly Glu His Thr Asp Leu Gly Lys Glu Gly Val Thr
1               5                   10                  15

Lys Gly Ala Asp Glu Leu Glu Lys Leu Phe Glu Ser Val Lys Asn Leu
            20                  25                  30

Ser Lys Ala Ala Lys Glu Met Leu Thr Asn Ser Val Lys Glu Ser Glu
        35                  40                  45

Lys Phe Ala Gly Lys Leu Lys Asn Glu His Ala Ser Leu Gly Lys Lys
    50                  55                  60

Asp Ala Thr Lys Gly Ala Lys Glu Leu Lys Asp Leu Ser Asp Ser Val
65                  70                  75                  80

Glu Ser Leu Val Lys Ala Ser Asp Asp Phe Thr Lys Lys Leu Gln Ser
                85                  90                  95

Ser His Ala Gln Leu Gly Val Ala Gly Gly Ala Thr Thr Ala Asp Glu
            100                 105                 110

Leu Glu Lys Leu Phe Lys Ser Val Glu Ser Leu Ala Lys Ala Ala Gln
        115                 120                 125

Asp Ala Leu Ala Asn Ser Val Asn Glu Leu Thr Ser Lys Lys Leu Lys
    130                 135                 140

Glu Lys His Thr Asp Leu Gly Lys Lys Asp Ala Thr Ala Ala Glu Leu
145                 150                 155                 160

Glu Lys Leu Phe Glu Ser Val Glu Asn Leu Ala Lys Ala Ala Lys Glu
                165                 170                 175

Met Leu Ser Asn Ser Asn Lys Ala Phe Thr Asp Lys Leu Lys Ser Ser
            180                 185                 190

His Ala Glu Leu Gly Ile Ala Asn Gly Ala Ala Thr Lys Gly Ala Gln
        195                 200                 205

Glu Leu Glu Lys Leu Phe Glu Ser Val Lys Asn Leu Ser Lys Ala Ala
    210                 215                 220

Gln Glu Thr Leu Asn Asn Ser Val Lys Glu Ser Glu Ser Phe Thr Lys
225                 230                 235                 240

Lys Leu Ser Asp Asn Gln Ala Glu Leu Gly Ile Glu Asn Ala Thr Lys
                245                 250                 255
```

-continued

```
Gly Ala Glu Glu Leu Val Lys Leu Ser Glu Ser Val Ala Gly Leu Leu
            260                 265                 270

Lys Ala Ala Gln Ala Ile Leu Ala Asn Ser Val Lys Glu Leu Thr Ser
        275                 280                 285

Pro Val Val Ala Glu Ser Pro Lys Lys Pro Asn Asn Ser Gly Lys Asp
    290                 295                 300

Gly Asn Thr Ser Ala Asn Ser Ala Asp Glu Ser Val Lys Gly Pro Asn
305                 310                 315                 320

Leu Thr Glu Ile Ser Lys Lys Ile Thr Glu Ser Asn Ala Val Val Leu
                325                 330                 335

Ala Val Lys Glu Ile Glu Thr Leu Leu Ser Ser Ile Asp Glu Leu Ala
            340                 345                 350

Thr Lys Ala Ile Gly Gln Lys Ile Asp Ala Asn Gly Leu Gly Val Gln
        355                 360                 365

Ala Asn Gln Asn Gly Ser Leu Leu Ala Gly Ala Tyr Ala Ile Ser Thr
    370                 375                 380

Leu Ile Thr Gln Lys Leu Ser Ala Leu Asn Ser Glu Asp Leu Lys Glu
385                 390                 395                 400

Lys Val Ala Lys Val Lys Lys Cys Ser Glu Asp Phe Thr Asn Lys Leu
                405                 410                 415

Lys Asn Gly Asn Ala Gln Leu Gly Leu Ala Ala Ala Thr Asp Asp Asn
            420                 425                 430

Ala Lys Ala Ala Ile Leu Lys Thr Asn Gly Thr Asn Asp Lys Gly Ala
        435                 440                 445

Lys Glu Leu Lys Asp Leu Ser Asp Ser Val Glu Ser Leu Val Lys Ala
    450                 455                 460

Ala Gln Val Met Leu Thr Asn Ser Val Lys Glu Leu Thr Ser Pro Val
465                 470                 475                 480

Val Ala Glu Ser Pro Lys Lys Pro
                485


<210> SEQ ID NO 32
<211> LENGTH: 190
<212> TYPE: PRT
<213> ORGANISM: Artificial Sequence
<220> FEATURE:
<223> OTHER INFORMATION: OspC phylotype F protein fragment

<400> SEQUENCE: 32

Asn Asn Ser Gly Lys Asp Gly Asn Thr Ser Ala Asn Ser Ala Asp Glu
1               5                   10                  15

Ser Val Lys Gly Pro Asn Leu Thr Glu Ile Ser Lys Lys Ile Thr Glu
            20                  25                  30

Ser Asn Ala Val Val Leu Ala Val Lys Glu Ile Glu Thr Leu Leu Ser
        35                  40                  45

Ser Ile Asp Glu Leu Ala Thr Lys Ala Ile Gly Gln Lys Ile Asp Ala
    50                  55                  60

Asn Gly Leu Gly Val Gln Ala Asn Gln Asn Gly Ser Leu Leu Ala Gly
65                  70                  75                  80

Ala Tyr Ala Ile Ser Thr Leu Ile Thr Gln Lys Leu Ser Ala Leu Asn
                85                  90                  95

Ser Glu Asp Leu Lys Glu Lys Val Ala Lys Val Lys Lys Cys Ser Glu
            100                 105                 110

Asp Phe Thr Asn Lys Leu Lys Asn Gly Asn Ala Gln Leu Gly Leu Ala
        115                 120                 125
```

-continued

```
Ala Ala Thr Asp Asp Asn Ala Lys Ala Ala Ile Leu Lys Thr Asn Gly
    130                 135                 140

Thr Asn Asp Lys Gly Ala Lys Glu Leu Lys Asp Leu Ser Asp Ser Val
145                 150                 155                 160

Glu Ser Leu Val Lys Ala Ala Gln Val Met Leu Thr Asn Ser Val Lys
                165                 170                 175

Glu Leu Thr Ser Pro Val Val Ala Glu Ser Pro Lys Lys Pro
            180                 185                 190


<210> SEQ ID NO 33
<211> LENGTH: 42
<212> TYPE: DNA
<213> ORGANISM: Artificial Sequence
<220> FEATURE:
<223> OTHER INFORMATION: primer

<400> SEQUENCE: 33

gacgacgaca agattgaata cattaagtgc aatattaatg ac                        42


<210> SEQ ID NO 34
<211> LENGTH: 52
<212> TYPE: DNA
<213> ORGANISM: Artificial Sequence
<220> FEATURE:
<223> OTHER INFORMATION: primer

<400> SEQUENCE: 34

gaggagaagc ccggtttaca aattaatctt ataatattga tcttaattaa gg             52


<210> SEQ ID NO 35
<211> LENGTH: 210
<212> TYPE: PRT
<213> ORGANISM: Borrelia burgdorferi

<400> SEQUENCE: 35

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Asp Ser Asn Ala Val Leu Leu Ala Val Lys Glu Val Glu Ala
    50                  55                  60

Leu Leu Ser Ser Ile Asp Glu Ile Ala Ala Lys Ala Ile Gly Lys Lys
65                  70                  75                  80

Ile His Gln Asn Asn Gly Leu Asp Thr Glu Asn Asn His Asn Gly Ser
                85                  90                  95

Leu Leu Ala Gly Ala Tyr Ala Ile Ser Thr Leu Ile Lys Gln Lys Leu
            100                 105                 110

Asp Gly Leu Lys Asn Glu Gly Leu Lys Glu Lys Ile Asp Ala Ala Lys
        115                 120                 125

Lys Cys Ser Glu Thr Phe Thr Asn Lys Leu Lys Glu Lys His Thr Asp
    130                 135                 140

Leu Gly Lys Glu Gly Val Thr Asp Ala Asp Ala Lys Glu Ala Ile Leu
145                 150                 155                 160

Lys Thr Asn Gly Thr Lys Thr Lys Gly Ala Glu Glu Leu Gly Lys Leu
                165                 170                 175

Phe Glu Ser Val Glu Val Leu Ser Lys Ala Ala Lys Glu Met Leu Ala
            180                 185                 190
```

Asn Ser Val Lys Glu Leu Thr Ser Pro Val Val Ala Glu Ser Pro Lys
195 200 205

Lys Pro
210

<210> SEQ ID NO 36
<211> LENGTH: 192
<212> TYPE: PRT
<213> ORGANISM: Borrelia burgdorferi

<400> SEQUENCE: 36

Asn Asn Ser Gly Lys Asp Gly Asn Thr Ser Ala Asn Ser Ala Asp Glu
1 5 10 15

Ser Val Lys Gly Pro Asn Leu Thr Glu Ile Ser Lys Lys Ile Thr Asp
20 25 30

Ser Asn Ala Val Leu Leu Ala Val Lys Glu Val Glu Ala Leu Leu Ser
35 40 45

Ser Ile Asp Glu Leu Ala Lys Ala Ile Gly Lys Lys Ile Lys Asn Asp
50 55 60

Gly Ser Leu Asp Asn Glu Ala Asn Arg Asn Glu Ser Leu Leu Ala Gly
65 70 75 80

Ala Tyr Thr Ile Ser Thr Leu Ile Thr Gln Lys Leu Ser Lys Leu Asn
85 90 95

Gly Ser Glu Gly Leu Lys Glu Lys Ile Ala Ala Ala Lys Lys Cys Ser
100 105 110

Glu Glu Phe Ser Thr Lys Leu Lys Asp Asn His Ala Gln Leu Gly Ile
115 120 125

Gln Gly Val Thr Asp Glu Asn Ala Lys Lys Ala Ile Leu Lys Ala Asn
130 135 140

Ala Ala Gly Lys Asp Lys Gly Val Glu Glu Leu Glu Lys Leu Ser Gly
145 150 155 160

Ser Leu Glu Ser Leu Ser Lys Ala Ala Lys Glu Met Leu Ala Asn Ser
165 170 175

Val Lys Glu Leu Thr Ser Pro Val Val Ala Glu Ser Pro Lys Lys Pro
180 185 190

<210> SEQ ID NO 37
<211> LENGTH: 192
<212> TYPE: PRT
<213> ORGANISM: Borrelia burgdorferi

<400> SEQUENCE: 37

Asn Asn Ser Gly Lys Asp Gly Asn Thr Ser Ala Asn Ser Ala Asp Glu
1 5 10 15

Ser Val Lys Gly Pro Asn Leu Thr Glu Ile Ser Lys Lys Ile Thr Asp
20 25 30

Ser Asn Ala Val Leu Leu Ala Val Lys Glu Val Glu Val Leu Leu Ser
35 40 45

Ser Ile Asp Glu Leu Ala Lys Lys Ala Ile Gly Lys Lys Ile Asp Gln
50 55 60

Asn Asn Ala Leu Gly Thr Leu Asn Asn His Asn Gly Ser Leu Leu Ala
65 70 75 80

Gly Ala Tyr Ala Ile Ser Ala Leu Ile Thr Glu Lys Leu Ser Ser Ile
85 90 95

Lys Asp Ser Gly Glu Leu Lys Ala Glu Ile Glu Lys Ala Lys Lys Cys
100 105 110

```
Ser Glu Ser Phe Thr Lys Lys Leu Ser Asp Asn Gln Ala Glu Leu Gly
        115                 120                 125

Ile Glu Asn Ala Thr Asp Asp Asn Ala Lys Lys Ala Ile Leu Lys Thr
    130                 135                 140

His Asn Ala Lys Asp Lys Gly Ala Glu Glu Leu Val Lys Leu Ser Glu
145                 150                 155                 160

Ser Val Ala Gly Leu Leu Lys Ala Ala Gln Ala Ile Leu Ala Asn Ser
                165                 170                 175

Val Lys Glu Leu Thr Ser Pro Val Val Ala Glu Ser Pro Lys Lys Pro
            180                 185                 190


<210> SEQ ID NO 38
<211> LENGTH: 187
<212> TYPE: PRT
<213> ORGANISM: Borrelia burgdorferi

<400> SEQUENCE: 38

Cys Asn Asn Ser Gly Lys Asp Gly Asn Ala Ser Ala Asn Ser Ala Asp
1               5                   10                  15

Glu Ser Val Lys Gly Pro Asn Leu Thr Glu Ile Ser Lys Lys Ile Thr
            20                  25                  30

Glu Ser Asn Ala Val Val Leu Ala Val Lys Glu Val Glu Thr Leu Leu
        35                  40                  45

Ala Ser Ile Asp Glu Leu Ala Thr Lys Ala Ile Gly Lys Lys Ile Gly
    50                  55                  60

Asn Asn Gly Leu Glu Ala Asn Gln Ser Lys Asn Thr Ser Leu Leu Ser
65                  70                  75                  80

Gly Ala Tyr Ala Ile Ser Asp Leu Ile Ala Glu Lys Leu Asn Val Leu
                85                  90                  95

Lys Asn Glu Glu Leu Lys Glu Lys Ile Asp Thr Ala Lys Gln Cys Ser
            100                 105                 110

Thr Glu Phe Thr Asn Lys Leu Lys Ser Glu His Ala Val Leu Gly Leu
        115                 120                 125

Asp Asn Leu Thr Asp Asp Asn Ala Gln Arg Ala Ile Leu Lys Lys His
    130                 135                 140

Ala Asn Lys Asp Lys Gly Ala Ala Glu Leu Glu Lys Leu Phe Lys Ala
145                 150                 155                 160

Val Glu Asn Leu Ser Lys Ala Ala Gln Asp Thr Leu Lys Asn Ala Val
                165                 170                 175

Lys Glu Leu Thr Ser Pro Ile Val Ala Glu Ser
            180                 185


<210> SEQ ID NO 39
<211> LENGTH: 187
<212> TYPE: PRT
<213> ORGANISM: Borrelia burgdorferi

<400> SEQUENCE: 39

Cys Asn Asn Ser Gly Lys Asp Gly Asn Thr Ser Ala Asn Ser Ala Asp
1               5                   10                  15

Glu Ser Val Lys Gly Pro Asn Leu Thr Glu Ile Ser Lys Lys Ile Thr
            20                  25                  30

Glu Ser Asn Ala Val Val Leu Ala Val Lys Glu Ile Glu Thr Leu Leu
        35                  40                  45

Ser Ser Ile Asp Glu Leu Ala Thr Lys Ala Ile Gly Gln Lys Ile Asp
    50                  55                  60
```

Ala Asn Gly Leu Gly Val Gln Ala Asn Gln Asn Gly Ser Leu Leu Ala
65 70 75 80

Gly Ala Tyr Ala Ile Ser Thr Leu Ile Thr Gln Lys Leu Ser Ala Leu
85 90 95

Asn Ser Glu Asp Leu Lys Glu Lys Val Ala Lys Val Lys Lys Cys Ser
100 105 110

Glu Asp Phe Thr Asn Lys Leu Lys Asn Gly Asn Ala Gln Leu Gly Leu
115 120 125

Ala Ala Ala Thr Asp Asp Asn Ala Lys Ala Ala Ile Leu Lys Thr Asn
130 135 140

Gly Thr Asn Asp Lys Gly Ala Lys Glu Leu Lys Asp Leu Ser Asp Ser
145 150 155 160

Val Glu Ser Leu Val Lys Ala Ala Gln Val Met Leu Thr Asn Ser Val
165 170 175

Lys Glu Leu Thr Ser Pro Val Val Ala Glu Ser
180 185

<210> SEQ ID NO 40
<211> LENGTH: 191
<212> TYPE: PRT
<213> ORGANISM: Borrelia burgdorferi

<400> SEQUENCE: 40

Asn Asn Ser Gly Lys Asp Gly Asn Thr Ser Ala Asn Ser Ala Asp Glu
1 5 10 15

Ser Val Lys Gly Pro Asn Leu Thr Glu Ile Ser Lys Lys Ile Thr Glu
20 25 30

Ser Asn Ala Val Val Leu Ala Val Lys Glu Val Glu Thr Leu Leu Ala
35 40 45

Ser Ile Asn Gln Leu Ala Lys Ala Ile Gly Lys Lys Ile Asp Gln Asn
50 55 60

Gly Thr Leu Gly Asp Asp Gly Gly Gln Asn Gly Ser Leu Leu Ala Gly
65 70 75 80

Ala Tyr Ala Ile Ser Thr Val Ile Ile Glu Lys Leu Ser Thr Leu Lys
85 90 95

Asn Val Glu Glu Leu Lys Glu Lys Ile Thr Lys Ala Lys Asp Cys Ser
100 105 110

Glu Lys Phe Ala Gly Lys Leu Lys Asn Glu His Ala Ser Leu Gly Lys
115 120 125

Lys Asp Ala Thr Asp Asp Asp Ala Lys Lys Ala Ile Leu Lys Thr His
130 135 140

Gly Asn Thr Asp Lys Gly Ala Lys Glu Leu Lys Asp Leu Ser Asp Ser
145 150 155 160

Val Glu Ser Leu Val Lys Ala Ala Lys Glu Met Leu Thr Asn Ser Val
165 170 175

Lys Glu Leu Thr Ser Pro Val Val Ala Glu Ser Pro Lys Lys Pro
180 185 190

<210> SEQ ID NO 41
<211> LENGTH: 210
<212> TYPE: PRT
<213> ORGANISM: Borrelia burgdorferi

<400> SEQUENCE: 41

Met Lys Lys Asn Thr Leu Ser Ala Ile Leu Met Thr Leu Phe Leu Phe
1 5 10 15

-continued

Ile Ser Cys Asn Asn Ser Gly Lys Asp Gly Asn Thr Ser Ala Asn Ser
20 25 30

Ala Asp Glu Ser Val Lys Gly Pro Asn Leu Thr Glu Ile Ser Lys Lys
35 40 45

Ile Thr Glu Ser Asn Ala Val Val Leu Ala Val Lys Glu Val Glu Thr
50 55 60

Leu Leu Thr Ser Ile Asp Glu Leu Ala Lys Ala Ile Gly Lys Lys Ile
65 70 75 80

Lys Asn Asp Val Ser Leu Asp Asn Glu Ala Asp His Asn Gly Ser Leu
85 90 95

Ile Ser Gly Ala Tyr Leu Ile Ser Thr Leu Ile Thr Lys Lys Ile Ser
100 105 110

Ala Ile Lys Asp Ser Gly Glu Leu Lys Ala Glu Ile Glu Lys Ala Lys
115 120 125

Lys Cys Ser Glu Glu Phe Thr Ala Lys Leu Lys Gly Glu His Thr Asp
130 135 140

Leu Gly Lys Glu Gly Val Thr Asp Asp Asn Ala Lys Lys Ala Ile Leu
145 150 155 160

Lys Thr Asn Asn Asp Lys Thr Lys Gly Ala Asp Glu Leu Glu Lys Leu
165 170 175

Phe Glu Ser Val Lys Asn Leu Ser Lys Ala Ala Lys Glu Met Leu Thr
180 185 190

Asn Ser Val Lys Glu Leu Thr Ser Pro Val Val Ala Glu Ser Pro Lys
195 200 205

Lys Pro
210

<210> SEQ ID NO 42
<211> LENGTH: 192
<212> TYPE: PRT
<213> ORGANISM: Borrelia burgdorferi

<400> SEQUENCE: 42

Asn Asn Ser Gly Lys Asp Gly Asn Thr Ser Ala Asn Ser Ala Asp Glu
1 5 10 15

Ser Val Lys Gly Pro Asn Leu Thr Glu Ile Ser Lys Lys Ile Thr Glu
20 25 30

Ser Asn Ala Val Val Leu Ala Val Lys Glu Ile Glu Thr Leu Leu Ala
35 40 45

Ser Ile Asp Glu Leu Ala Thr Lys Ala Ile Gly Lys Lys Ile Gln Gln
50 55 60

Asn Gly Gly Leu Ala Val Glu Ala Gly His Asn Gly Thr Leu Leu Ala
65 70 75 80

Gly Ala Tyr Thr Ile Ser Lys Leu Ile Thr Gln Lys Leu Asp Gly Leu
85 90 95

Lys Asn Ser Glu Lys Leu Lys Glu Lys Ile Glu Asn Ala Lys Lys Cys
100 105 110

Ser Glu Asp Phe Thr Lys Lys Leu Glu Gly Glu His Ala Gln Leu Gly
115 120 125

Ile Glu Asn Val Thr Asp Glu Asn Ala Lys Lys Ala Ile Leu Ile Thr
130 135 140

Asp Ala Ala Lys Asp Lys Gly Ala Ala Glu Leu Glu Lys Leu Phe Lys
145 150 155 160

Ala Val Glu Asn Leu Ala Lys Ala Ala Lys Glu Met Leu Ala Asn Ser

```
                165                 170                 175

Val Lys Glu Leu Thr Ser Pro Ile Val Ala Glu Ser Pro Lys Lys Pro
            180                 185                 190


<210> SEQ ID NO 43
<211> LENGTH: 202
<212> TYPE: PRT
<213> ORGANISM: Borrelia burgdorferi

<400> SEQUENCE: 43

Ser Ala Ile Leu Met Thr Leu Phe Leu Phe Ile Ser Cys Asn Asn Ser
1               5                   10                  15

Gly Lys Asp Gly Asn Ala Ser Val Asn Ser Ala Asp Glu Ser Val Lys
            20                  25                  30

Gly Pro Asn Leu Val Glu Ile Ser Lys Lys Ile Thr Asp Ser Asn Ala
        35                  40                  45

Val Val Ile Ala Val Lys Glu Val Glu Thr Leu Leu Val Ser Ile Asp
    50                  55                  60

Glu Leu Ala Lys Ala Ile Gly Lys Lys Ile Glu Ala Gly Gly Thr Leu
65                  70                  75                  80

Gly Ser Asp Gly Ala His Asn Gly Ser Leu Leu Ala Gly Ala Tyr Lys
                85                  90                  95

Ile Ala Thr Glu Ile Thr Ala Asn Leu Ser Lys Leu Lys Ala Ser Glu
            100                 105                 110

Asp Leu Lys Glu Lys Ile Thr Lys Ala Lys Glu Cys Ser Glu Lys Phe
        115                 120                 125

Thr Asp Lys Leu Lys Ser Glu Asn Ala Ala Leu Gly Lys Gln Asp Ala
    130                 135                 140

Ser Asp Asp Asp Ala Lys Lys Ala Ile Leu Lys Thr His Asn Asp Ile
145                 150                 155                 160

Thr Lys Gly Ala Lys Glu Leu Lys Glu Leu Ser Glu Ser Val Glu Thr
                165                 170                 175

Leu Leu Lys Ala Ala Lys Glu Met Leu Ala Asn Ser Val Lys Glu Leu
            180                 185                 190

Thr Ser Pro Val Val Ala Lys Asn Pro Lys
        195                 200


<210> SEQ ID NO 44
<211> LENGTH: 212
<212> TYPE: PRT
<213> ORGANISM: Borrelia burgdorferi

<400> SEQUENCE: 44

Met Lys Lys Asn Thr Leu Ser Ala Ile Leu Met Thr Leu Phe Leu Phe
1               5                   10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Glu Ser Asn Ala Val Val Leu Ala Val Lys Glu Val Glu Thr
    50                  55                  60

Leu Leu Ala Ser Ile Asp Glu Val Ala Lys Lys Ala Ile Gly Asn Leu
65                  70                  75                  80

Ile Ala Gln Asn Gly Leu Asn Ala Gly Ala Asn Gln Asn Gly Ser Leu
                85                  90                  95

Leu Ala Gly Ala Tyr Val Ile Ser Thr Leu Ile Ala Glu Lys Leu Asp
```

-continued

```
            100                 105                 110

Gly Leu Lys Asn Ser Glu Glu Leu Lys Glu Lys Ile Glu Asp Ala Lys
        115                 120                 125

Lys Cys Asn Lys Ala Phe Thr Asp Lys Leu Lys Ser Ser His Ala Glu
    130                 135                 140

Leu Gly Ile Ala Asn Gly Ala Ala Thr Asp Ala Asn Ala Lys Ala Ala
145                 150                 155                 160

Ile Leu Lys Thr Asn Gly Thr Lys Asp Lys Gly Ala Gln Glu Leu Glu
                165                 170                 175

Lys Leu Phe Glu Ser Val Lys Asn Leu Ser Lys Ala Ala Gln Glu Thr
            180                 185                 190

Leu Asn Asn Ser Val Lys Glu Leu Thr Ser Pro Val Val Ala Glu Ser
        195                 200                 205

Pro Lys Lys Pro
    210


<210> SEQ ID NO 45
<211> LENGTH: 192
<212> TYPE: PRT
<213> ORGANISM: Borrelia burgdorferi

<400> SEQUENCE: 45

Asn Asn Ser Gly Lys Asp Gly Asn Ala Ser Thr Asn Ser Ala Asp Glu
1               5                   10                  15

Ser Val Lys Gly Pro Asn Leu Thr Glu Ile Ser Lys Lys Ile Thr Glu
            20                  25                  30

Ser Asn Ala Val Val Leu Ala Val Lys Glu Val Ala Ala Leu Leu Ser
        35                  40                  45

Ser Ile Asp Glu Leu Ala Lys Ala Ile Gly Lys Lys Ile Asn Asn Asn
    50                  55                  60

Gly Leu Asp Asp Val Gln Asn Phe Asn Ala Ser Leu Leu Ala Gly Ala
65                  70                  75                  80

His Thr Ile Ser Lys Leu Val Thr Glu Lys Leu Ser Lys Leu Lys Asn
                85                  90                  95

Ser Glu Gly Leu Lys Glu Lys Ile Glu Asp Ala Lys Lys Cys Ser Asp
            100                 105                 110

Asp Phe Thr Lys Lys Leu Gln Ser Ser His Ala Gln Leu Gly Val Ala
        115                 120                 125

Gly Gly Ala Thr Thr Asp Glu Glu Ala Lys Lys Ala Ile Leu Arg Thr
    130                 135                 140

Asn Ala Ile Lys Asp Lys Gly Ala Asp Glu Leu Glu Lys Leu Phe Lys
145                 150                 155                 160

Ser Val Glu Ser Leu Ala Lys Ala Ala Gln Asp Ala Leu Ala Asn Ser
                165                 170                 175

Val Asn Glu Leu Thr Ser Pro Val Val Ala Glu Ser Pro Lys Lys Pro
            180                 185                 190


<210> SEQ ID NO 46
<211> LENGTH: 191
<212> TYPE: PRT
<213> ORGANISM: Borrelia burgdorferi

<400> SEQUENCE: 46

Cys Asn Asn Ser Gly Lys Asp Gly Asn Ala Ser Ala Asn Ser Ala Asp
1               5                   10                  15

Glu Ser Val Lys Gly Pro Asn Leu Ala Glu Ile Ser Lys Lys Ile Thr
```

-continued

```
            20                  25                  30

Glu Ser Asn Ala Val Val Leu Ala Val Lys Glu Val Glu Ala Leu Leu
        35                  40                  45

Ala Ser Ile Asp Glu Ile Gly Ser Lys Ala Ile Gly Lys Arg Ile Gln
    50                  55                  60

Ala Asn Gly Leu Gln Asp Leu Gln Gly Gln Asn Gly Ser Leu Leu Ala
65                  70                  75                  80

Gly Ala Tyr Ala Ile Ser Asn Leu Ile Thr Gln Lys Ile Asn Val Leu
                85                  90                  95

Asn Gly Leu Lys Asn Ser Glu Glu Leu Lys Glu Lys Ile Asn Glu Ala
            100                 105                 110

Lys Gly Cys Ser Glu Lys Phe Thr Lys Lys Leu Ser Glu Ser His Ala
        115                 120                 125

Asp Ile Gly Ile Gln Ala Ala Thr Asp Ala Asn Ala Lys Asp Ala Ile
    130                 135                 140

Leu Lys Thr Asn Pro Thr Lys Thr Lys Gly Ala Glu Glu Leu Asp Lys
145                 150                 155                 160

Leu Phe Lys Ala Val Glu Asn Leu Ser Lys Ala Ala Lys Glu Met Leu
                165                 170                 175

Ala Asn Ser Val Lys Glu Leu Thr Ser Pro Val Val Ala Glu Ser
            180                 185                 190


<210> SEQ ID NO 47
<211> LENGTH: 6
<212> TYPE: PRT
<213> ORGANISM: Artificial Sequence
<220> FEATURE:
<223> OTHER INFORMATION: hexa-histidine peptide

<400> SEQUENCE: 47

His His His His His His
1               5
```